US006218123B1

United States Patent
Nehls et al.

(10) Patent No.: US 6,218,123 B1
(45) Date of Patent: Apr. 17, 2001

(54) CONSTRUCTION OF NORMALIZED CDNA LIBRARIES FROM EUCARYOTIC CELLS

(75) Inventors: Michael Nehls; Brian Zambrowicz; Glenn Friedrich, all of The Woodlands, TX (US); H. Earl Ruley, Nashville, TN (US); Arthur T. Sands; Sigrid Wattler, both of The Woodlands, TX (US)

(73) Assignee: Lexicon Genetics Incorporated, The Woodlands, TX (US)

( * ) Notice: Subject to any disclaimer, the term of this patent is extended or adjusted under 35 U.S.C. 154(b) by 0 days.

(21) Appl. No.: 09/371,257

(22) Filed: Aug. 10, 1999

Related U.S. Application Data

(60) Provisional application No. 60/095,989, filed on Aug. 10, 1998.

(51) Int. Cl.[7] .............................. C12Q 1/68; C12N 15/63; C12N 15/11
(52) U.S. Cl. ...................... 435/6; 435/172.3; 435/320.1; 536/24.2; 536/23.1
(58) Field of Search .................. 435/6, 172.3, 320.1; 536/24.2, 23.1

(56) References Cited

U.S. PATENT DOCUMENTS

| | | | |
|---|---|---|---|
| 5,506,126 | * | 4/1996 | Seed et al. ........................ 435/172.3 |
| 5,556,772 | | 9/1996 | Sorge et al. . |
| 5,646,009 | * | 7/1997 | Rhoads et al. ....................... 435/69.1 |

FOREIGN PATENT DOCUMENTS

| | | |
|---|---|---|
| WO 98/14614 | 4/1998 | (WO) . |
| WO 99/50426 | 10/1999 | (WO) . |

OTHER PUBLICATIONS

Rossouw CM et al, "DNA sequences in the first intron of the huyman pro–alpha 1(I) collagen gene enhance trancription", Journal of Biological Chemistry, Nov. 5, 1987, vol. 262, No. 31, pp. 15151–15157.*

Sasaki K et al, "Cloning and expression of a complementary DNA encoding a bovine adrenal angiotensin II type–1 receptor", Nature, vol. 351, May 16, 1991, pp. 230–233.*

Yin Jingwen et al, "Stable transfection of Acanthamoeba", Can. J. Microbiol, vol. 43, 1997, pp. 239–244.*

Nehls et al., "Exon amplification from complete libraries of genomic DNA using a novel phage vector with automatic plasmid excision facility: application to the mouse neurofibromatosis–1 locus," *Oncogene*, 9:2169–2175 (1994).

Nehls et al., "The sequence complexity of exons trapped from the mouse genome," *Current Biology*, 4(11):983–989 (1994).

Yoshida et al., "A new strategy of gene trapping in ES cells using 3'RACE," *Transgenic Research*, 4:277–287 (1995).

Zambrowicz et al., "Disruption and sequence identification of 2,000 genes in mouse embryonic stem cells," *Nature*, 392:608–611 (1998).

Zambrowicz et al., "Comprehensive mammalian genetics: history and future prospects of gene trapping in the mouse," *Int. J. Dev. Biol.*, 42:1025–1036 (1998).

* cited by examiner

*Primary Examiner*—John S. Brusca
*Assistant Examiner*—Stephen Siu
(74) *Attorney, Agent, or Firm*—Finnegan, Henderson, Farabow, Garrett & Dunner, L.L.P.

(57) ABSTRACT

A new technology is described that allows for the rapid and efficient construction of complex cDNA libraries from cultured eukaryotic cells. The technology exploits eukaryotic biology by using transgenic constructs that have been nonspecifically inserted into the genome to facilitate the expression of nuclear genes as fusion transcripts. The invention further allows one to specifically subclone the corresponding fusion transcripts into highly complex cDNA libraries. The libraries are easily characterized by molecular analysis techniques such as hybridization, and individual clones can be directly sequenced to generate a sequence database of the cellular portion of the fusion transcripts.

9 Claims, 17 Drawing Sheets

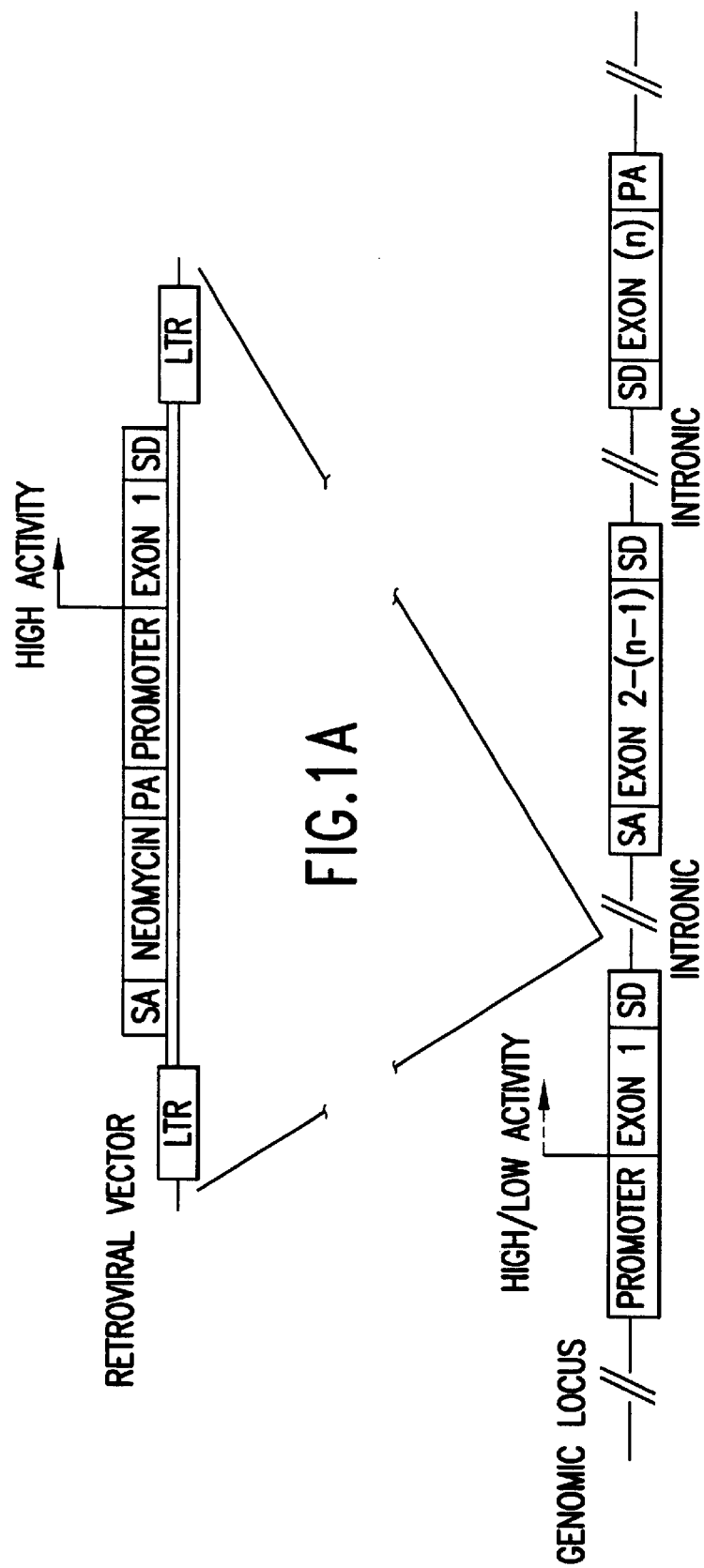

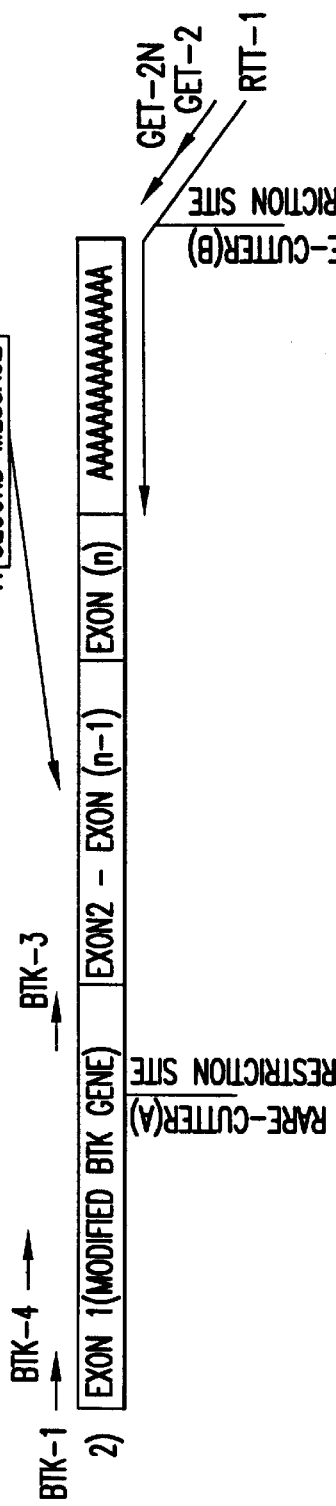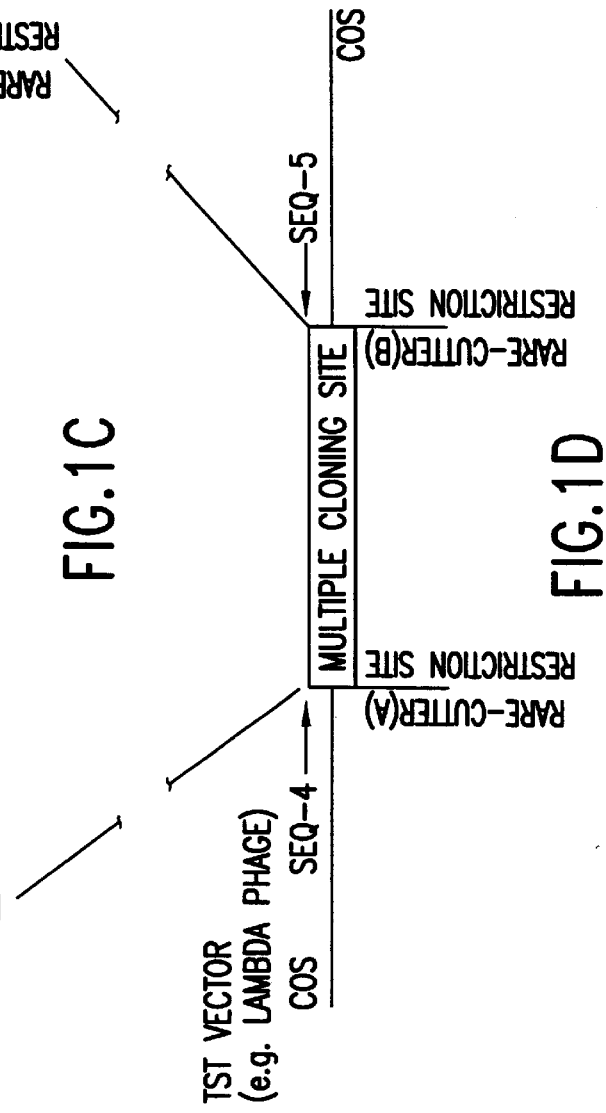
FIG.1C
FIG.1D

HIGH-THROUGHPUT GENE TRAPPING IN PLANTS

TRANSPOSON MEDIATED GENE TRAPPING: THE ACTIVATOR/DISSOCIATION (Ac/Ds) SYSTEM

- MAIZE        McCLINTOCK B.        CARNEGIE INST. WASH. 47:155 (1948) AND 48:148 (1949)
- TOBACCO      BAKER ET AL.         PROC. NATL. ACAD. SCI. USA 83:4844 (1986)
- *ARABIDOPSIS* NUSSAUME ET AL.     MOL. GEN. GENET. 249:91 (1995)
- CARROT       VAN SLUYS ET AL.     EMBO J. 6:3881 (1987)
- SOYBEAN      ZHOU AND ATHERLY     PLANT CELL REP. 8:542 (1990)
- POTATO       KNAPP ET AL          MOL. GEN. GENET. 213:285 (1988)

| HCST / HTST | LENGTH | ACCESSION NUMBER | DEFINITION | E VALUE (% I.D.) |
|---|---|---|---|---|
| •HCST1554 HTST5056 | 758 | •P05813 (sp) BEST! | sp:HOMO SAPIENS BETA CRYSTALLIN A3 [CONTAINS: BETA CRYSTALLIN A1] [ALIGNMENT] [ABSTRACT] [ABSTRACT] | 1.0e-105 (99%) |
| •HCST1575 HTST5124 | 550 | •Q13508 (sp) BEST! | sp:HOMO SAPIENS TESTIS ECTO-ADP-RIBOSYLTRANSFERASE PRECURSOR (EC 2.4.2.3.1) (TESTISNAD(P)(+)--ARGININE ADP-RIBOSYLTRANSFERASE)(TESTIS MONO(ADP-RIBOSYL) TRANSFERASE) [ALIGNMENT] [ABSTRACT] [ABSTRACT] | 1.0e-100 (99%) |
| •HCST1605 HTST5208 | 572 | •P47224 (sp) BEST! | sp:HOMO SAPIENS GUANINE NUCLEOTIDE EXCHANGE FACTOR MSS4 [ALIGNMENT] [ABSTRACT] [ABSTRACT] | 2.0e-44 (100%) |
| •HCST1741 HTST5602 | 437 | •P17075 (sp) BEST! | sp:HOMO SAPIENS 40S RIBOSOMAL PROTEIN S20 [ALIGNMENT] [ABSTRACT] [ABSTRACT] | 2.0e-58 (100%) |
| •HCST1776 HTST5700 | 965 | •P04646 (sp) BEST! | sp:RATTUS NORVEGICUS 60S RIBOSOMAL PROTEIN L35A [ALIGNMENT] [ABSTRACT] | 2.0e-56 (97%) |
| •HCST1800 HTST5782 | 446 | •P23396 (sp) BEST! | sp:HOMO SAPIENS 40S RIBOSOMAL PROTEIN S3 [ALIGNMENT] [ABSTRACT] [ABSTRACT] [ABSTRACT] | 2.0e-58 (100%) |
| •HCST1803 HTST5794 | 593 | •P17544 (sp) BEST! | sp:HOMO SAPIENS TRANSCRIPTION FACTOR ATF-A AND ATF-A-DELTA [ALIGNMENT] [ABSTRACT] | 1.0e-42 (100%) |
| •HCST1807 HTST5800 | 531 | •Q15102 (sp) BEST! | sp:HOMO SAPIENS PLATELET-ACTIVATING FACTOR ACETYLHYDROLASE IB GAMMA SUBUNIT(EC 3.1.1.47) (PAF ACETYLHYDROLASE 29 KD SUBUNIT) (PAF-AH 29 KDSUBUNIT) (PAF-AH GAMMA SUBUNIT) [ALIGNMENT] [ABSTRACT] | 7.0e-84 (97%) |
| •HCST1837 HTST5887 | 773 | •P02608 (sp) BEST! | sp:ORYCTOLAGUS CUNICULUS MYOSIN REGULATORY LIGHT CHAIN 2, SKELETAL MUSCLE ISOFORM TYPE 2 (G2)(DTNB) (MLC-2) [ALIGNMENT] [ABSTRACT] [ABSTRACT] [ABSTRACT] [ABSTRACT] | 7.0e-90 (96%) |
| •HCST1844 HTST5904 | 616 | •P15154 (sp) BEST! | sp:HOMO SAPIENS RAS-RELATED C3 BOTULINUM TOXIN SUBSTRATE 1 (P21-RAC1) (RAS-LIKEPROTEIN TC25) [ALIGNMENT] [ABSTRACT] [ABSTRACT] [ABSTRACT] [ABSTRACT] [ABSTRACT] [ABSTRACT] | 2.0e-91 (98%) |
| •HCST1877 HTST6036 | 588 | •Q06830 (sp) BEST! | sp:HOMO SAPIENS THIOREDOXIN PEROXIDASE 2 (THIOREDOXIN-DEPENDENT PEROXIDE REDUCTASE 2)(PROLIFERATION-ASSOCIATED PROTEIN PAG) (NATURAL KILLER CELL ENHANCINGFACTOR A) (NKEF-A) [ALIGNMENT] [ABSTRACT] [ABSTRACT] | 4.0e-88 (100%) |
| •HCST1919 HTST6139 | 584 | •Q14088 (sp) BEST! | sp:HOMO SAPIENS SMALL GTP-BINDING PROTEIN S10 [ALIGNMENT] [ABSTRACT] | 6.0e-86 (100%) |
| •HCST2095 HTST6738 | 505 | •P13284 (sp) BEST! | sp:HOMO SAPIENS GAMMA-INTERFERON-INDUCIBLE PROTEIN IP-30 PRECURSOR [ALIGNMENT] [ABSTACT] | 4.0e-62 (96%) |
| •HCST2155 HTST6864 | 836 | •P49720 (sp) BEST! | sp:HOMO SAPIENS PROTEASOME THETA CHAIN (EC 3.4.99.46) (MACROPAIN THETA CHAIN) (MULTICATALYTIC ENDOPEPTIDASE COMPLEX THETA CHAIN) (PROTEASOMECHAIN 13) (PROTEASOME COMPONENT C10-II) [ALIGNMENT] [ABSTRACT] [ABSTRACT] | 1.0e-116 (100%) |
| •HCST2163 HTST6883 | 772 | •P18282 (sp) BEST! | sp:HOMO SAPIENS DESTRIN (ACTIN DEPOLYMERIZING FACTOR) (ADF) [ALIGNMENT] [ABSTRACT] [ABSTRACT] [ABSTRACT] | 9.0e-91 (98%) |

FIG.4A

| HCST / HTST | LENGTH | ACCESSION NUMBER | DEFINITION | E VALUE (% I.D.) |
|---|---|---|---|---|
| •HCST2169 HTST6900 | 784 | •P19105 (sp) BEST! | sp:HOMO SAPIENS MYOSIN REGULATORY LIGHT CHAIN 2, NONSARCOMERIC (MYOSIN RLC) [ALIGNMENT] [ABSTRACT] | 2.0e-86 (99%) |
| •HCST2183 HTST6945 | 520 | •P78537 (sp) BEST! | sp:HOMO SAPIENS RT14 PROTEIN (GCN5-LIKE PROTEIN 1) [ALIGNMENT] [ABSTRACT] [ABSTRACT] | 1.0e-45 (100%) |
| •HCST2206 HTST7007 | 738 | •P55809 (sp) BEST! | sp:HOMO SAPIENS SUCCINYL-COA:3-KETOACID-COENZYME A TRANSFERASE PRECURSOR (EC 2.8.3.5)(SUCCINYL COA:3-OXOACID COA-TRANSFERASE) (OXCT) [ALIGNMENT] [ABSTRACT] [ABSTRACT] | 2.0e-84 (100%) |
| •HCST2208 HTST7015 | 453 | •P35658 (sp) BEST! | sp:HOMO SAPIENS NUCLEAR PORE COMPLEX PROTEIN NUP214 (NUCLEOPORIN NUP214) (214 KDNUCLEOPORIN) (CAN PROTEIN) [ALIGNMENT] [ABSTRACT] [ABSTRACT] | 8.0e-76 (99%) |
| •HCST2256 HTST7151 | 769 | •P31949 (sp) BEST! | sp:HOMO SAPIENS CALGIZZARIN (S100C PROTEIN) (MLN70) [ALIGNMENT] [ABSTRACT] [ABSTRACT] [ABSTRACT] | 1.0e-54 (100%) |
| •HCST2276 HTST7228 | 770 | •P49773 (sp) BEST! | sp:HOMO SAPIENS HINT PROTEIN (PROTEIN KINASE C INHIBITOR 1) (PKCI-1) [ALIGNMENT] [ABSTRACT] [ABSTRACT] [ABSTRACT] | 1.0e-47 (99%) |
| •HCST2287 HTST7262 | 778 | •Q16719 (sp) BEST! | sp:HOMO SAPIENS KYNURENINASE (EC 3.7.1.3)(L-KYNURENINE HYDROLASE) [ALIGNMENT] [ABSTRACT] [ABSTRACT] | 9.0e-64 (100%) |
| •HCST2386 HTST7503 | 875 | •P15559 (sp) BEST! | sp:HOMO SAPIENS NAD(P)H DEHYDROGENASE (QUINONE) 1 (EC 1.6.99.2) (QUINONE REDUCTASE)(DT-DIAPHORASE) (AZOREDUCTASE) (PHYLLOQUINONE REDUCTASE) (MENADIONEREDUCTASE) [ALIGNMENT] [ABSTRACT] [ABSTRACT] | 6.0e-61 (96%) |
| •HCST2389 HTST7511 | 594 | •P48645 (sp) BEST! | sp:HOMO SAPIENS NEUROMEDIN U-25 PRECURSOR (NMU-25) [ALIGNMENT] [ABSTRACT] | 2.0e-43 (98%) |
| •HCST2402 HTST7542 | 466 | •P16587 (sp) BEST! | sp:HOMO SAPIENS ADP-RIBOSYLATION FACTOR 3 [ALIGNMENT] [ABSTRACT] [ABSTRACT] [ABSTACT] | 2.0e-61 (100%) |
| •HCST2430 HTST7632 | 665 | •P50461 (sp) BEST! | sp:HOMO SAPIENS LIM DOMAIN PROTEIN, CARDIAC (MUSCLE LIM PROTEIN) (CYSTEINE-RICHPROTEIN 3) (CRP3) (LIM-ONLY PROTEIN 4) [ALIGNMENT] [ABSTRACT] | 1.0e-117 (98%) |
| •HCST2482 HTST7761 | 508 | •P09527 (sp) BEST! | sp:RATTUS NORVEGICUS RAS-RELATED PROTEIN RAB-7 (RAS-RELATED PROTEIN P23) (RAS-RELATEDPROTEIN BRL-RAS) [ALIGNMENT] [ABSTRACT] | 1.0e-97 (98%) |
| •HCST2496 HTST7799 | 614 | •Q08722 (sp) BEST! | sp:HOMO SAPIENS LEUKOCYTE SURFACE ANTIGEN CD47 PRECURSOR (ANTIGENIC SURFACEDETERMINANT PROTEIN OA3) (INTEGRIN ASSOCIATED PROTEIN) (IAP) (MER6) [ALIGNMENT] [ABSTRACT] [ABSTRACT] [ABSTRACT] | 1.0e-147 (99%) |
| •HCST2542 HTST7931 | 427 | •P12280 (sp) BEST! | sp:CANIS FAMILIARIS MICROSOMAL SIGNAL PEPTIDASE 23 KD SUBUNIT (EC 3.4.-.-) (SPC22/23) [ALIGNMENT] [ABSTRACT] | 2.0e-74 (100%) |
| •HCST2572 HTST8023 | 1063 | •P52788 (sp) BEST! | sp:HOMO SAPIENS SPERMINE SYNTHASE (EC 2.5.1.22) (SPERMIDINE AMINOPROPYLTRANSFERASE) [ALIGNMENT] [ABSTRACT] | 1.0e-125 (97%) |

FIG.4B

| HCST HTST | LENGTH | ACCESSION NUMBER | DEFINITION | E VALUE (% I.D.) |
|---|---|---|---|---|
| •HCST2617 HTST8139 | 697 | •P56134 (sp) BEST! | sp:HOMO SAPIENS ATP SYNTHASE F CHAIN, MITOCHONDRIAL (EC 3.6.1.34) [ALIGNMENT] [ABSTRACT] [ABSTRACT] [ABSTRACT] | 4.0e-46 (100%) |
| •HCST2632 HTST8182 | 902 | •P27348 (sp) BEST! | sp:HOMO SAPIENS 14-3-3 PROTEIN TAU (14-3-3 PROTEIN THETA) (14-3-3 PROTEIN T-CELL) (HS1 PROTEIN) [ALIGNMENT] [ABSTRACT] [ABSTRACT] [ABSTRACT] | 3.0e-71 (99%) |
| •HCST2647 HTST8214 | 712 | •Q29375 (sp) BEST! | sp:SUS SCROFA 60S RIBOSOMAL PROTEIN L7A (SURFEIT LOCUS PROTEIN 3) (FRAGMENT) [ALIGNMENT] [ABSTRACT] | 2.0e-61 (98%) |
| •HCST2740 HTST8461 | 603 | •P50053 (sp) BEST! | sp:HOMO SAPIENS KETOHEXOKINASE (EC 2.7.1.3) (HEPATIC FRUCTOKINASE) [ALIGNMENT] [ABSTRACT] | 1.0e-100 (97%) |
| •HCST2750 HTST8482 | 734 | •Q14188 (sp) BEST! | sp:HOMO SAPIENS TRANSCRIPTION FACTOR DP-2 (E2F DIMERIZATION PARTNER 2) [ALIGNMENT] [ABSTRACT] [ABSTRACT] | 1.0e-58 (100%) |
| •HCST2758 HTST8514 | 545 | •P04643 (sp) BEST! | sp:HOMO SAPIENS 40S RIBOSOMAL PROTEIN S11 [ALIGNMENT] [ABSTRACT] [ABSTRACT] | 7.0e-79 (97%) |
| •HCST2947 HTST9127 | 541 | •P55010 (sp) BEST! | sp:HOMO SAPIENS EUKARYOTIC TRANSLATION INITIATION FACTOR 5 (EIF-5) [ALIGNMENT] | 1.0e-54 (96%) |
| •HCST2990 HTST9252 | 505 | •P05162 (sp) BEST! | sp:HOMO SAPIENS GALECTIN-2 (BETA-GALACTOSIDE-BINDING LECTIN L-14-II) (LACTOSE-BINDINGLECTIN 2) (S-LAC LECTIN 2) (HL14) [ALIGNMENT] [ABSTRACT] [ABSTRACT] [ABSTRACT] [ABSTRACT] | 3.0e-74 (99%) |
| •HCST3062 HTST9528 | 649 | •P39019 (sp) BEST! | sp:HOMO SAPIENS 40S RIBOSOMAL PROTEIN S19 [ALIGNMENT] [ABSTRACT] | 2.0e-79 (100%) |
| •HCST3135 HTST9757 | 789 | •P02278 (sp) BEST! | sp:HOMO SAPIENS HISTONE H2B (H2B.1 A) [ALIGNMENT] [ABSTRACT] [ABSTRACT] [ABSTRACT] | 2.0e-44 (100%) |
| •HCST3169 HTST9844 | 549 | •P52209 (sp) BEST! | sp:HOMO SAPIENS 6-PHOSPHOGLUCONATE DEHYDROGENASE, DECARBOXYLATING (EC 1.1.1.44) [ALIGNMENT] [ABSTRACT] | 2.0e-68 (98%) |
| •HCST3225 HTST10041 | 573 | •P46405 (sp) BEST! | sp:SUS SCROFA 40S RIBOSOMAL PROTEIN S12 [ALIGNMENT] [ABSTRACT] | 2.0e-68 (96%) |
| •HCST3310 HTST10342 | 453 | •P52758 (sp) BEST! | sp:HOMO SAPIENS 14.5 KD TRANSLATIONAL INHIBITOR PROTEIN (P14.5) (UK114 ANTIGENHOMOLOG) [ALIGNMENT] [ABSTRACT] | 2.0e-55 (99%) |
| •HCST3358 HTST10614 | 539 | •P25120 (sp) BEST! | sp:HOMO SAPIENS 60S RIBOSOMAL PROTEIN L8 [ALIGNMENT] [ABSTRACT] [ABSTRACT] | 1.0e-86 (99%) |
| •HCST3364 HTST10665 | 437 | •Q12934 (sp) BEST! | sp:HOMO SAPIENS FILENSIN (LENS FIBER CELL BEADED-FILAMENT STRUCTURAL PROTEIN CP115)(CP115) (LENS INTERMEDIATE FILAMENT LIKE-HEAVY) (LIFL-H) (FRAGMENT) [ALIGNMENT] [ABSTRACT] | 3.0e-46 (96%) |

FIG.4C

| HCST / HTST | LENGTH | ACCESSION NUMBER | DEFINITION | E VALUE (% I.D.) |
|---|---|---|---|---|
| •HCST3396 HTST10805 | 608 | •075828 (sp) BEST! | sp:HOMO SAPIENS CARBONYL REDUCTASE [NADPH] 3 (EC 1.1.1.184) (NADPH-DEPENDENT CARBONYLREDUCTASE 3) [ALIGNMENT] [ABSTRACT] | 4.0e-87 (100%) |
| •HCST3453 HTST11116 | 520 | •P24311 (sp) BEST! | sp:HOMO SAPIENS CYTOCHROME C OXIDASE POLYPEPTIDE VIIB PRECURSOR (EC 1.9.3.1) [ALIGNMENT] [ABSTRACT] [ABSTRACT] | 3.0e-42 (97%) |
| •HCST3491 HTST11269 | 568 | •P06351 (sp) BEST! | sp:HOMO SAPIENS HISTONE H3.3 (H3.B) (H3.3Q) [ALIGNMENT] [ABSTRACT] [ABSTRACT] [ABSTRACT] [ABSTRACT] [ABSTRACT] [ABSTRACT] [ABSTRACT] [ABSTRACT] [ABSTRACT] [ABSTRACT] | 4.0e-66 (96%) |
| •HCST3497 HTST11280 | 470 | •P07316 (sp) BEST! | sp:HOMO SAPIENS GAMMA CRYSTALLIN B (GAMMA CRYSTALLIN 1-2) [ALIGNMENT] [ABSTRACT] [ABSTRACT] | 5.0e-50 (100%) |
| •HCST3501 HTST11292 | 827 | •P09661 (sp) BEST! | sp:HOMO SAPIENS U2 SMALL NUCLEAR RIBONUCLEOPROTEIN A' (U2 SNRNP-A') [ALIGNMENT] [ABSTRACT] | 4.0e-99 (100%) |
| •HCST3535 HTST11428 | 355 | •P02350 (sp) BEST! | sp:XENOPUS LAEVIS 40S RIBOSOMAL PROTEIN S3A (S1A) [ALIGNMENT] [ABSTRACT] [ABSTRACT] | 1.0e-57 (98%) |
| •HCST3578 HTST11616 | 571 | •P11249 (sp) BEST! | sp:RATTUS NORVEGICUS 60S RIBOSOMAL PROTEIN L18A [ALIGNMENT] [ABSTRACT] | 6.0e-95 (99%) |
| •HCST3586 HTST11647 | 516 | •P08579 (sp) BEST! | sp:HOMO SAPIENS U2 SMALL NUCLEAR RIBONUCLEOPROTEIN B'' [ALIGNMENT] [ABSTRACT] | 1.0e-54 (100%) |
| •HCST3630 HTST11861 | 653 | •P53480 (sp) BEST! | sp:FUGU RUBRIPES ACTIN, ALPHA CARDIAC [ALIGNMENT] [ABSTRACT] | 5.0e-70 (96%) |
| •HCST3865 HTST13402 | 641 | •Q16181 (sp) BEST! | sp:HOMO SAPIENS CDC10 PROTEIN HOMOLOG [ALIGNMENT] [ABSTRACT] | 3.0e-74 (96%) |
| •HCST3937 HTST13682 | 686 | •P16930 (sp) BEST! | sp:HOMO SAPIENS FUMARYLACETOACETASE (EC 3.7.1.2) (FUMARYLACETOACETATE HYDROLASE)(BETA-DIKETONASE) (FAA) [ALIGNMENT] [ABSTRACT] [ABSTRACT] [ABSTRACT] [ABSTRACT] [ABSTRACT] [ABSTRACT] [ABSTRACT] [ABSTRACT] [ABSTRACT] | 1.0e-110 (99%) |
| •HCST3970 HTST13830 | 686 | •Q16550 (sp) BEST! | sp:HOMO SAPIENS TRANSCRIPTION INITIATION PROTEIN SPT4 HOMOLOG 1 [ALIGNMENT] [ABSTRACT] | 4.0e-63 (98%) |
| •HCST4102 HTST14558 | 640 | •P09237 (sp) BEST! | sp:HOMO SAPIENS MATRILYSIN PRECURSOR (EC 3.4.24.23) (PUMP-1 PROTEASE) (UTERINEMETALLOPROTEINASE) (MATRIX METALLOPROTEINASE-7) (MMP-7) (MATRIN) [ALIGNMENT] [ABSTRACT] [ABSTRACT] [ABSTRACT] [ABSTRACT] [ABSTRACT] [ABSTRACT] [ABSTRACT] | 1.0e-108 (98%) |
| •HCST4144 HTST14758 | 603 | •P54296 (sp) BEST! | sp:HOMO SAPIENS M-PROTEIN (165 KD TITIN-ASSOCIATED PROTEIN) (165 KD CONNECTIN-ASSOCIATED PROTEIN) [ALIGNMENT] [ABSTRACT] | 7.0e-88 (99%) |
| •HCST4177 HTST14953 | 564 | •P41250 (sp) BEST! | sp:HOMO SAPIENS GLYCYL-TRNA SYNTHETASE (EC 6.1.1.14) (GLYCINE --TRNA LIGASE) (GLYRS) [ALIGNMENT] [ABSTRACT] [ABSTRACT] [ABSTRACT] | 7.0e-89 (100%) |

FIG.4D

| HCST / HTST | LENGTH | ACCESSION NUMBER | DEFINITION | E VALUE (% I.D.) |
|---|---|---|---|---|
| •HCST4250 HTST15349 | 565 | •P25325 (sp) BEST! | sp:HOMO SAPIENS 3-MERCAPTOPYRUVATE SULFURTRANSFERASE (EC 2.8.1.2) (MST) [ALIGNMENT] [ABSTRACT] | 2.0e-51 (100%) |
| •HCST4258 HTST15444 | 597 | •P36969 (sp) BEST! | sp:HOMO SAPIENS PHOSPHOLIPID HYDROPEROXIDE GLUTATHIONE PEROXIDASE (EC 1.11.1.9)(PHGPX) [ALIGNMENT] [ABSTRACT] | 7.0e-94 (97%) |
| •HCST4305 HTST15879 | 682 | •P10301 (sp) BEST! | sp:HOMO SAPIENS RAS-RELATED PROTEIN R-RAS (P23) [ALIGNMENT] [ABSTRACT] | 4.0e-93 (99%) |
| •HCST4511 HTST16751 | 598 | •P43251 (sp) BEST! | sp:HOMO SAPIENS BIOTINIDASE PRECURSOR (EC 3.5.1.12) [ALIGNMENT] [ABSTRACT] [ABSTRACT] | 2.0e-75 (99%) |
| •HCST4605 HTST17177 | 1097 | •P24572 (sp) BEST! | sp:HOMO SAPIENS MYOSIN LIGHT CHAIN ALKALI, SMOOTH-MUSCLE ISOFORM (MLC3SM) (LC17B) (LC17-GI) [ALIGNMENT] [ABSTRACT] [ABSTRACT] [ABSTRACT] | 1.0e-78 (96%) |
| •HCST4838 HTST18284 | 370 | •O75380 (sp) BEST! | sp:HOMO SAPIENS NADH-UBIQUINONE OXIDOREDUCTASE 13 KD-A SUBUNIT PRECURSOR (EC 1.6.5.3) (EC 1.6.99.3) (COMPLEX I-13KD-A) (CI-13KD-A) [ALIGNMENT] [ABSTRACT] | 6.0e-43 (99%) |
| •HCST5006 HTST19030 | 458 | •O00483 (sp) BEST! | sp:HOMO SAPIENS NADH-UBIQUINONE OXIDOREDUCTASE MLRQ SUBUNIT (EC 1.6.5.3) (EC 1.6.99.3) (COMPLEX I-MLRQ) (CI-MLRQ) [ALIGNMENT] [ABSTRACT] | 3.0e-44 (100%) |
| •HCST5056 HTST19287 | 579 | •Q99865 (sp) BEST! | sp:HOMO SAPIENS SPINDLIN HOMOLOG (PROTEIN DXF34) [ALIGNMENT] | 5.0e-94 (99%) |
| •HCST5059 HTST19332 | 623 | •Q00380 (sp) BEST! | sp:MUS MUSCULUS CLATHRIN COAT ASSEMBLY PROTEIN AP17 (CLATHRIN COAT ASSOCIATED PROTEINAP17) (PLASMA MEMBRANE ADAPTOR AP-2 17 KD PROTEIN) (HA2 17 KD SUBUNIT)(CLATHRIN ASSEMBLY PROTEIN 2 SMALL CHAIN) [ALIGNMENT] [ABSTRACT] | 1.0e-72 (100%) |
| •HCST5064 HTST19354 | 664 | •O15482 (sp) BEST! | sp:HOMO SAPIENS TESTIS-SPECIFIC PROTEIN TEX28 [ALIGNMENT] [ABSTRACT] | 2.0e-84 (97%) |
| •HCST5182 HTST20122 | 848 | •P01266 (sp) BEST! | sp:HOMO SAPIENS THYROGLOBULIN PRECURSOR [ALIGNMENT] [ABSTRACT] [ABSTRACT] [ABSTRACT] [ABSTRACT] [ABSTRACT] [ABSTACT] [ABSTRACT] | 1.0e-77 (99%) |
| •HCST5184 HTST20136 | 374 | •P14854 (sp) BEST! | sp:HOMO SAPIENS CYTOCHROME C OXIDASE POLYPEPTIDE VIB (EC 1.9.3.1) (AED) [ALIGNMENT] [ABSTRACT] [ABSTRACT] [ABSTRACT] [ABSTRACT] | 2.0e-49 (100%) |
| •HCST5186 HTST20139 | 610 | •P35265 (sp) BEST! | sp:HOMO SAPIENS 40S RIBOSOMAL PROTEIN S21 [ALIGNMENT] [ABSTRACT] | 6.0e-42 (100%) |
| •HCST5239 HTST20350 | 581 | •P02735 (sp) BEST! | sp:HOMO SAPIENS SERUM AMYLOID A PROTEIN PRECURSOR [ALIGNMENT] [ABSTRACT] [ABSTRACT] [ABSTRACT] [ABSTRACT] [ABSTRACT] [ABSTRACT] [ABSTRACT] [ABSTRACT] [ABSTRACT] [ABSTRACT] [ABSTRACT] | 5.0e-68 (98%) |
| •HCST5416 HTST21322 | 1172 | •P07195 (sp) BEST! | sp:HOMO SAPIENS L-LACTATE DEHYDROGENASE H CHAIN (EC 1.1.1.27) (LDH-B) [ALIGNMENT] [ABSTRACT] [ABSTRACT] [ABSTRACT] [ABSTRACT] [ABSTRACT] [ABSTRACT] | 1.0e-170 (97%) |

FIG.4E

| HCST / HTST | LENGTH | ACCESSION NUMBER | DEFINITION | E VALUE (% I.D.) |
|---|---|---|---|---|
| •HCST5433 / HTST21425 | 537 | •P30040 (sp) BEST! | sp:HOMO SAPIENS ENDOPLASMIC RETICULUM PROTEIN ERP29 PRECURSOR (ERP31) (ERP28) [ALIGNMENT] [ABSTRACT] [ABSTRACT] [ABSTRACT] | 2.0e-68 (95%) |
| •HCST5505 / HTST21808 | 663 | •O15144 (sp) BEST! | sp:HOMO SAPIENS ARP2/3 COMPLEX 34 KD SUBUNIT (P34-ARC) [ALIGNMENT] [ABSTRACT] [ABSTRACT] | 1.0e-114 (98%) |
| •HCST5506 / HTST21813 | 417 | •P06493 (sp) BEST! | sp:HOMO SAPIENS CELL DIVISION CONTROL PROTEIN 2 HOMOLOG (EC 2.7.1.-) (P34 PROTEINKINASE) (CYCLIN-DEPENDENT KINASE 1) (CDK1) [ALIGNMENT] [ABSTRACT] [ABSTRACT] | 4.0e-69 (96%) |
| •HCST5512 / HTST21825 | 594 | •P51654 (sp) BEST! | sp:HOMO SAPIENS GLYPICAN-3 PRECURSOR (INTESTINAL PROTEIN OCI-5) (GTR2-2) (MXR7) [ALIGNMENT] [ABSTRACT] | 1.0e-101 (96%) |
| •HCST5514 / HTST21832 | 593 | •P25121 (sp) BEST! | sp:RATTUS NORVEGICUS 60S RIBOSOMAL PROTEIN L11 [ALIGNMENT] [ABSTRACT] | 5.0e-94 (99%) |
| •HCST5531 / HTST21911 | 574 | •P23528 (sp) BEST! | sp:HOMO SAPIENS COFILIN, NON-MUSCLE ISOFORM [ALIGNMENT] [ABSTRACT] [ABSTRACT] | 2.0e-90 (99%) |
| •HCST5577 / HTST22067 | 473 | •Q16394 (sp) BEST! | sp:HOMO SAPIENS EXOSTOSIN-1 (PUTATIVE TUMOUR SUPPRESSOR PROTEIN EXT1) (MULTIPLEEXOSTOSES PROTEIN 1) [ALIGNMENT] [ABSTRACT] [ABSTRACT] [ABSTRACT] | 1.0e-69 (100%) |
| •HCST5583 / HTST22095 | 566 | •P49368 (sp) BEST! | sp:HOMO SAPIENS T-COMPLEX PROTEIN 1, GAMMA SUBUNIT (TCP-1-GAMMA) (CCT-GAMMA) [ALIGNMENT] [ABSTRACT] [ABSTRACT] | 8.0e-91 (100%) |
| •HCST5587 / HTST22115 | 538 | •P56519 (sp) BEST! | sp:GALLUS GALLUS HISTONE DEACETYLASE 2 (HD2) [ALIGNMENT] | 1.0e-103 (98%) |
| •HCST5589 / HTST22123 | 816 | •Q16394 (sp) BEST! | sp:HOMO SAPIENS EXOSTOSIN-1 (PUTATIVE TUMOUR SUPPRESSOR PROTEIN EXT1) (MULTIPLEEXOSTOSES PROTEIN 1) [ALIGNMENT] [ABSTRACT] [ABSTRACT] [ABSTRACT] | 1.0e-99 (99%) |
| •HCST5612 / HTST22233 | 470 | •P08238 (sp) BEST! | sp:HOMO SAPIENS HEAT SHOCK PROTEIN HSP 90-BETA (HSP 84) (HSP 90) [ALIGNMENT] [ABSTRACT] [ABSTRACT] [ABSTRACT] [ABSTRACT] [ABSTRACT] [ABSTRACT] | 2.0e-67 (95%) |
| •HCST5633 / HTST22367 | 512 | •P07900 (sp) BEST! | sp:HOMO SAPIENS HEAT SHOCK PROTEIN HSP 90-ALPHA (HSP 86) (AED) [ALIGNMENT] [ABSTRACT] [ABSTRACT] [ABSTRACT] [ABSTRACT] [ABSTRACT] [ABSTRACT] [ABSTRACT] [ABSTRACT] | 2.0e-80 (100%) |
| •HCST5656 / HTST22478 | 600 | •P45880 (sp) BEST! | sp:HOMO SAPIENS VOLTAGE-DEPENDENT ANION-SELECTIVE CHANNEL PROTEIN 2 (VDAC2) (OUTER MITOCHONDRIAL MEMBRANE PROTEIN PORIN) [ALIGNMENT] [ABSTRACT] [ABSTRACT] | 1.0e-59 (100%) |
| •HCST5665 / HTST22529 | 438 | •O00567 (sp) BEST! | sp:HOMO SAPIENS NUCLEOLAR PROTEIN NOP56 [ALIGNMENT] | 3.0e-46 (100%) |
| •HCST5846 / HTST23393 | 569 | •P35287 (sp) BEST! | sp:RATTUS NORVEGICUS RAS-RELATED PROTEIN RAB-14 [ALIGNMENT] [ABSTRACT] | 4.0e-90 (95%) |

FIG.4F

| HCST / HTST | LENGTH | ACCESSION NUMBER | DEFINITION | E VALUE (% I.D.) |
|---|---|---|---|---|
| •HCST5885 HTST23572 | 682 | •Q16698 (sp) BEST! | sp:HOMO SAPIENS 2,4-DIENOYL-COA REDUCTASE, MITOCHONDRIAL PRECURSOR (EC 1.3.1.34) (2,4-DIENOYL-COA REDUCTASE [NADPH]) [ALIGNMENT] [ABSTRACT] [ABSTRACT] | 1.0e-111 (98%) |
| •HCST6060 HTST24513 | 558 | •P08206 (sp) BEST! | sp:HOMO SAPIENS CALPACTIN I LIGHT CHAIN (P10 PROTEIN) (P11) (CELLULAR LIGAND OF ANNEXIN II) [ALIGNMENT] [ABSTRACT] [ABSTRACT] [ABSTRACT] [ABSTRACT] [ABSTRACT] | 6.0e-52 (100%) |
| •HCST6159 HTST25266 | 678 | •P37058 (sp) BEST! | sp:HOMO SAPIENS ESTRADIOL 17 BETA-DEHYDROGENASE 3 (EC 1.1.1.62) (17-BETA-HSD 3) (TESTICULAR 17-BETA-HYDROXYSTEROID DEHYDROGENASE) [ALIGNMENT] [ABSTRACT] [ABSTRACT] | 1.0e-110 (99%) |
| •HCST6199 HTST25617 | 370 | •P36954 (sp) BEST! | sp:HOMO SAPIENS DNA-DIRECTED RNA POLYMERASE II 14.5 KD POLYPEPTIDE (EC 2.7.7.6)(RPB9) (RPB14.5) [ALIGNMENT] [ABSTRACT] | 1.0e-56 (100%) |
| •HCST6422 HTST26888 | 612 | •Q92503 (sp) BEST! | sp:HOMO SAPIENS SEC14-LIKE PROTEIN [ALIGNMENT] [ABSTRACT] | 2.0e-87 (97%) |
| •HCST6476 HTST27150 | 562 | •P55197 (sp) BEST! | sp:HOMO SAPIENS AF-10 PROTEIN [ALIGNMENT] [ABSTRACT] | 7.0e-43 (95%) |
| •HCST6477 HTST27151 | 698 | •Q01658 (sp) BEST! | sp:HOMO SAPIENS TATA-BINDING PROTEIN-ASSOCIATED PHOSPHOPROTEIN (DOWN-REGULATOR OF TRANSCRIPTION 1) (DR1 PROTEIN) [ALIGNMENT] [ABSTRACT] | 2.0e-44 (100%) |
| •HCST6614 HTST27833 | 806 | •Q16831 (sp) BEST! | sp:HOMO SAPIENS URIDINE PHOSPHORYLASE (EC 2.4.2.3) (UDRPASE) [ALIGNMENT] [ABSTRACT] | 4.0e-88 (99%) |
| •HCST6624 HTST27887 | 477 | •Q63769 (sp) BEST! | sp:RATTUS NORVEGICUS SUSHI REPEAT-CONTAINING PROTEIN SRPX PRECURSOR (DRS PROTEIN (DOWN-REGULATED BY V-SRC) [ALIGNMENT] [ABSTRACT] | 7.0e-68 (97%) |
| •HCST6766 HTST28743 | 549 | •P15374 (sp) BEST! | sp:HOMO SAPIENS UBIQUITIN CARBOXYL-TERMINAL HYDROLASE ISOZYME L3 (EC 3.1.2.15) (UCH-L3) (UBIQUITIN THIOLESTERASE L3 [ALIGNMENT] [ABSTRACT] [ABSTRACT] | 2.0e-78 (97%) |
| •HCST6819 HTST29060 | 654 | •P51161 (sp) BEST! | sp:HOMO SAPIENS GASTROTROPIN (GT) (ILEAL LIPID-BINDING PROTEIN) (ILBP) (INTESTINAL 15KD PROTEIN) (I-15P) (INTESTINAL BILE ACID-BINDING PROTEIN) (I-BABP) [ALIGNMENT] [ABSTRACT] | 2.0e-65 (95%) |
| •HCST6844 HTST29356 | 675 | •P18085 (sp) BEST! | sp:HOMO SAPIENS ADP-RIBOSYLATION FACTOR 4 [ALIGNMENT] [ABSTRACT] [ABSTRACT] | 7.0e-88 (100%) |
| •HCST6864 HTST29560 | 496 | •P21181 (sp) BEST! | sp:HOMO SAPIENS G25K GTP-BINDING PROTEIN, BRAIN ISOFORM (GP) (CDC42 HOMOLOG) [ALIGNMENT] [ABSTRACT] [ABSTRACT] [ABSTRACT] [ABSTRACT] | 1.0e-81 (99%) |
| •HCST6866 HTST29583 | 982 | •P49393 (sp) BEST! | sp:XENOPUS LAEVIS 40S RIBOSOMAL PROTEIN S13 [ALIGNMENT] | 4.0e-66 (100%) |
| •HCST6874 HTST29643 | 517 | •P09417 (sp) BEST! | sp:HOMO SAPIENS DIHYDROPTERIDINE REDUCTASE (EC 1.6.99.7) (HDHPR) (QUINOID DIHYDROPTERIDINE REDUCTASE) [ALIGNMENT] [ABSTRACT] [ABSTRACT] [ABSTRACT] [ABSTRACT] [ABSTRACT] [ABSTRACT] [ABSTRACT] | 7.0e-53 (100%) |

FIG.4G

| HCST / HTST | LENGTH | ACCESSION NUMBER | DEFINITION | E VALUE (% I.D.) |
|---|---|---|---|---|
| •HCST6884 HTST29733 | 483 | •P42704 (sp) BEST! | sp:HOMO SAPIENS 130 KD LEUCINE-RICH PROTEIN (LRP 130) (GP130) [ALIGNMENT] [ABSTRACT] | 4.0e-64 (97%) |
| •HCST6928 HTST30176 | 576 | •P50991 (sp) BEST! | sp:HOMO SAPIENS T-COMPLEX PROTEIN 1, DELTA SUBUNIT (TCP-1-DELTA) (CCT-DELTA)(STIMULATOR OF TAR RNA BINDING) [ALIGNMENT] [ABSTRACT] | 3.0e-76 (97%) |
| •HCST6929 HTST30206 | 776 | •P11169 (sp) BEST! | sp:HOMO SAPIENS GLUCOSE TRANSPORTER TYPE 3, BRAIN [ALIGNMENT] [ABSTRACT] | 1.0e-129 (97%) |
| •HCST7093 HTST31003 | 485 | •O43708 (sp) BEST! | sp:HOMO SAPIENS MALEYLACETOACETATE ISOMERASE (EC 5.2.1.2) (MAAI) (GLUTATHIONETRANSFERASE ZETA 1) (EC 2.5.1.18) [ALIGNMENT] [ABSTRACT] [ABSTRACT] | 4.0e-78 (98%) |
| •HCST7103 HTST31061 | 611 | •P56377 (sp) BEST! | sp:HOMO SAPIENS CLATHRIN COAT ASSEMBLY PROTEIN AP19 (CLATHRIN COAT ASSOCIATED PROTEINAP19) (GOLGI ADAPTOR AP-1 19 KD ADAPTIN) (HA1 19 KD SUBUNIT) (CLATHRINASSEMBLY PROTEIN COMPLEX 1 SMALL CHAIN) [ALIGNMENT] | 2.0e-76 (100%) |
| •HCST7116 HTST31096 | 597 | •P49119 (sp) BEST! | sp:MESOCRICETUS AURATUS PUTATIVE ORAL CANCER SUPPRESSOR (DELETED IN ORAL CANCER-1) [ALIGNMENT] [ABSTRACT] | 1.0e-47 (98%) |
| •HCST7217 HTST31122 | 972 | •P39023 (sp) BEST! | sp:HOMO SAPIENS 60S RIBOSOMAL PROTEIN L3 (HIV-1 TAR RNA BINDING PROTEIN B) (TARBP-B) [ALIGNMENT] [ABSTRACT] | 1.0e-169 (95%) |
| •HCST7154 HTST31200 | 603 | •P56519 (sp) BEST! | sp:GALLUS GALLUS HISTONE DEACETYLASE 2 (HD2) [ALIGNMENT] | 1.0e-107 (97%) |
| •HCST7174 HTST31264 | 788 | •O00299 (sp) BEST! | sp:HOMO SAPIENS CHLORIDE INTRACELLULAR CHANNEL PROTEIN 1 (NUCLEAR CHLORIDE ION CHANNEL27) (P64 CLCP) [ALIGNMENT] [ABSTRACT] | 1.0e-120 (97%) |
| •HCST7194 HTST31304 | 717 | •P51669 (sp) BEST! | sp:HOMO SAPIENS UBIQUITIN-CONJUGATING ENZYME E2-17 KD 2 (EC 6.3.2.19) (UBIQUITIN-PROTEIN LIGASE) (UBIQUITIN CARRIER PROTEIN) (E2(17)KB 2) [ALIGNMENT] [ABSTRACT] [ABSTACT] [ABSTRACT] [ABSTRACT] | 3.0e-84 (98%) |
| •HCST7274 HTST31567 | 670 | •P35218 (sp) BEST! | sp:HOMO SAPIENS CARBONIC ANHYDRASE V PRECURSOR (EC 4.2.1.1) (CARBONATE DEHYDRATASEV) [ALIGNMENT] [ABSTRACT] | 1.0e-106 (98%) |
| •HCST7310 HTST31700 | 461 | •P49585 (sp) BEST! | sp:HOMO SAPIENS CHOLINEPHOSPHATE CYTIDYLYLTRANSFERASE (EC 2.7.7.15) (PHOSPHORYLCHOLINETRANSFERASE) (CT) [ALIGNMENT] [ABSTRACT] | 5.0e-73 (96%) |
| •HCST7316 HTST31717 | 514 | •Q61990 (sp) BEST! | sp:MUS MUSCULUS PUTATIVE HETEROGENEOUS NUCLEAR RIBONUCLEO-PROTEIN X (HNRNP X) (CBP) [ALIGNMENT] [ABSTRACT] [ABSTRACT] | 1.0e-48 (100%) |
| •HCST7384 HTST32021 | 528 | •P07992 (sp) BEST! | sp:HOMO SAPIENS DNA EXCISION REPAIR PROTEIN ERCC-1 [ALIGNMENT] [ABSTRACT] [ABSTRACT] [ABSTRACT] | 3.0e-95 (99%) |
| •HCST7408 HTST32162 | 614 | •Q64311 (sp) BEST! | sp:MUS MUSCULUS PROTEIN N-TERMINAL ASPARAGINE AMIDOHYDROLASE (EC 3.5.1.-) (PROTEINNH2-TERMINAL ASPARAGINE DEAMIDASE) (NTN-AMIDASE) (PNAD) (PROTEIN NH2-TERMINAL ASPARAGINE AMIDOHYDROLASE) (PNAA) [ALIGNMENT] [ABSTRACT] | 10e-102 (95%) |

FIG.4H

| HCST HTST | LENGTH | ACCESSION NUMBER | DEFINITION | E VALUE (% I.D.) |
|---|---|---|---|---|
| •HCST7421 HTST32246 | 547 | •P29372 (sp) BEST! | sp:HOMO SAPIENS DNA-3-METHYLADENINE GLYCOSIDASE (EC 3.2.2.21) (3-METHYLADENINE DNAGLYCOSYLASE) (ADPG) (3-ALKYLADENINE DNA GLYCOSYLASE) (N-METHYLPURINE-DNA GLYCOSIRASE) [ALIGNMENT] [ABSTRACT] [ABSTRACT] [ABSTRACT] | 2.0e-95 (95%) |
| •HCST7432 HTST32302 | 553 | •P00568 (sp) BEST! | sp:HOMO SAPIENS ADENYLATE KINASE ISOENZYME 1 (EC 2.7.4.3) (ATP-AMP TRANSPHOSPHORYLASE)(AK1) (MYOKINASE) [ALIGNMENT] [ABSTRACT] [ABSTRACT] | 5.0e-81 (100%) |
| •HCST7554 HTST32876 | 539 | •P20674 (sp) BEST! | sp:HOMO SAPIENS CYTOCHROME C OXIDASE POLYPEPTIDE VA PRECURSOR (EC 1.9.3.1) [ALIGNMENT] [ABSTRACT] [ABSTRACT] [ABSTRACT] | 1.0e-62 (98%) |
| •HCST7702 HTST33883 | 621 | •P05323 (sp) BEST! | sp:HOMO SAPIENS SERINE/THREONINE PROTEIN PHOSPHATASE PP2A-ALPHA, CATALYTIC SUBUNIT(EC 3.1.3.16) [ALIGNMENT] [ABSTRACT] [ABSTRACT] [ABSTRACT] [ABSTRACT] [ABSTRACT] [ABSTRACT] | 1.0e-106 (99%) |
| •HCST7709 HTST33919 | 562 | •P26516 (sp) BEST! | sp:MUS MUSCULUS 26S PROTEASOME REGULATORY SUBUNIT S12 (PROTEASOME SUBUNIT P40) (MOV34PROTEIN) [ALIGNMENT] [ABSTRACT] [ABSTRACT] | 1.0e-79 (98%) |
| •HCST7730 HIST34066 | 764 | •Q14192 (sp) BEST! | sp:HOMO SAPIENS SKELETAL MUSCLE LIM-PROTEIN 3 (SLIM 3) (LIM-DOMAIN PROTEIN DRAL)(FOUR AND A HALF LIM DOMAINS PROTEIN 2) (FHL-2) [ALIGNMENT] [ABSTRACT] [ABSTRACT] | 1.0e-153 (100%) |
| •HCST7784 HTST34290 | 420 | •Q15404 (sp) BEST! | sp:HOMO SAPIENS RAS SUPPRESSOR PROTEIN 1 (RSU-1) (RSP-1 PROTEIN) (RSP-1) [ALIGNMENT] [ABSTRACT] | 6.0e-72 (97%) |
| •HCST7831 HTST34524 | 757 | •P00505 (sp) BEST! | sp:HOMO SAPIENS ASPARTATE AMINOTRANSFERASE, MITOCHONDRIAL PRECURSOR (EC 2.6.1.1) (TRANSAMINASE A) (GLUTAMATE OXALOACETATE TRANSAMINASE-2) [ALIGNMENT] [ABSTRACT] [ABSTRACT] | 2.0e-64 (100%) |
| •HCST7851 HTST34601 | 463 | •Q61142 (sp) BEST! | sp:MUS MUSCULUS SPINDLIN (30000 MR METAPHASE COMPLEX) (SSEC P) [ALIGNMENT] [ABSTRACT] | 1.0e-60 (97%) |
| •HCST7854 HTST34610 | 645 | •P23381 (sp) BEST! | sp:HOMO SAPIENS TRYPTOPHANYL-TRNA SYNTHETASE (EC 6.1.1.2) (TRYPTOPHAN--TRNA LIGASE)(TRPRS) (IFP53) [ALIGNMENT] [ABSTRACT] [ABSTRACT] [ABSTRACT] [ABSTRACT] [ABSTRACT] | 2.0e-95 (97%) |
| •HCST7871 HTST34692 | 756 | •P35080 (sp) BEST! | sp:HOMO SAPIENS PROFILIN II [ALIGNMENT] [ABSTRACT] | 5.0e-46 (100%) |
| •HCST7878 HTST34748 | 434 | •P50613 (sp) BEST! | sp:HOMO SAPIENS CELL DIVISION PROTEIN KINASE 7 (EC 2.7.1.-) (CDK-ACTIVATING KINASE)(CAK) (39 KD PROTEIN KINASE) (P39 MO15) (STK1) (CAK1) [ALIGNMENT] [ABSTRACT] [ABSTRACT] [ABSTRACT] [ABSTRACT] [ABSTRACT] | 3.0e-71 (96%) |
| •HCST7884 HTST34799 | 725 | •P54105 (sp) BEST! | sp:HOMO SAPIENS CHLORIDE CONDUCTANCE REGULATORY PROTEIN ICLN (CHLORIDE CHANNEL, NUCLEOTIDE SENSITIVE 1A) (CHOLORIDE ION CURRENT INDUCER PROTEIN) (CLCI) (RETICULOCYTE PICLN) [ALIGNMENT] [ABSTRACT] [ABSTRACT] [ABSTRACT] | 5.0e-76 (99%) |

FIG.41-1

| | | | | |
|---|---|---|---|---|
| •HCST8045<br>HTST35906 | 460 | •P42655<br>(sp) BEST! | sp:HOMO SAPIENS 14-3-3 PROTEIN EPSILON (MITOCHONDRIAL IMPORT STIMULATION FACTOR LSUBUNIT) (PROTEIN KINASE C INHIBITOR PROTEIN-1) (KCIP-1) (14-3-3E) [ALIGNMENT] [ABSTRACT] [ABSTRACT] [ABSTRACT] [ABSTRACT] [ABSTRACT] [ABSTRACT] [ABSTRACT] [ABSTRACT] [ABSTRACT] | 6.0e-69<br>(100%) |
| •HCST8133<br>HTST42746 | 694 | •Q13361<br>(sp) BEST! | sp:HOMO SAPIENS MICROFIBRIL-ASSOCIATED GLYCOPROTEIN 2 PRECURSOR (MAGP-2) (MP25) [ALIGNMENT] [ABSTRACT] | 3.0e-80<br>(99%) |

FIG.41-2

| HCST HTST | LENGTH | ACCESSION NUMBER | DEFINITION | E VALUE (% I.D.) |
|---|---|---|---|---|
| •HCST8188 HTST29772 | 789 | •P06351 (sp) BEST! | sp:HOMO SAPIENS HISTONE H3.3 (H3.B) (H3.3Q) [ALIGNMENT] [ABSTRACT] [ABSTRACT] [ABSTRACT] [ABSTRACT] [ABSTRACT] [ABSTRACT] [ABSTRACT] [ABSTRACT] [ABSTRACT] [ABSTRACT] [ABSTRACT] | 3.0e-70 (100%) |
| •HCST8219 HTST37041 | 448 | •Q28824 (sp) BEST! | sp:BOS TAURUS MYOSIN LIGHT CHAIN KINASE, SMOOTH MUSCLE (EC 2.7.1.117) (MLCK)[CONTAINS: TELOKIN] [ALIGNMENT] [ABSTRACT] | 5.0e-84 (99%) |
| •HCST8222 HTST37052 | 721 | •P05127 (sp) BEST! | sp:HOMO SAPIENS PROTEIN KINASE C, BETA-II TYPE (EC 2.7.1.-)(PKC-BETA-2) [ALIGNMENT] [ABSTRACT] [ABSTRACT] [ABSTRACT] [ABSTRACT] | 1.0e-117 (95%) |
| •HCST8288 HTST37349 | 570 | •P19087 (sp) BEST! | sp:HOMO SAPIENS GUANINE NUCLEOTIDE-BINDING PROTEIN G(T), ALPHA-2 SUBUNIT (TRANSDUCINALPHA-2 CHAIN) [ALIGNMENT] [ABSTRACT] [ABSTRACT] [ABSTRACT] | 5.0e-75 (99%) |
| •HCST8413 HTST38063 | 348 | •P25120 (sp) BEST! | sp:HOMO SAPIENS 60S RIBOSOMAL PROTEIN L8 [ALIGNMENT] [ABSTRACT] [ABSTRACT] | 9.0e-52 (99%) |
| •HCST8417 HTST38172 | 504 | •P08578 (sp) BEST! | sp:HOMO SAPIENS U1 AND U2 SMALL NUCLEAR RIBONUCLEOPROTEIN E (SNRNP-E) [ALIGNMENT] [ABSTRACT] [ABSTRACT] [ABSTRACT] | 6.0e-41 (100%) |
| •HCST8440 HTST38368 | 671 | •P52434 (sp) BEST! | sp:HOMO SAPIENS DNA-DIRECTED RNA POLYMERASES I, II, AND III 17.1 KD POLYPEPTIDE(EC 2.7.7.6) (RPB17) (RPB8) [ALIGNMENT] [ABSTRACT] [ABSTRACT] | 1.0e-64 (97%) |
| •HCST8448 HTST38406 | 541 | •P18708 (sp) BEST! | sp:CRICETULUS GRISEUS VESICULAR-FUSION PROTEIN NSF (N-ETHYLMALEIMIDE-SENSITIVE FUSIONPROTEIN) (NEM-SENSITIVE FUSION PROTEIN) [ALIGNMENT] [ABSTRACT] [ABSTRACT] [ABSTRACT] [ABSTRACT] | 2.0e-69 (98%) |
| •HCST8457 HTST38479 | 718 | •P32780 (sp) BEST! | sp:HOMO SAPIENS BASIC TRANSCRIPTION FACTOR 62 KD SUBUNIT (P62) [ALIGNMENT] [ABSTRACT] | 1.0e-61 (97%) |
| •HCST8480 HTST38619 | 616 | •P12815 (sp) BEST! | sp:MUS MUSCULUS PROBABLE CALCIUM-BINDING PROTEIN ALG-2 (PMP41) (ALG-257) [ALIGNMENT] [ABSTRACT] [ABSTRACT] | 1.0e-83 (99%) |
| •HCST8573 HTST39322 | 457 | •P55145 (sp) BEST! | sp:HOMO SAPIENS ARGININE-RICH PROTEIN [ALIGNMENT] | 5.0e-84 (99%) |
| •HCST8865 HTST41574 | 514 | •P05413 (sp) BEST! | sp:HOMO SAPIENS FATTY ACID-BINDING PROTEIN, HEART (H-FABP) (MUSCLE FATTY ACID-BINDINGPROTEIN) (M-FABP) (MAMMARY-DERIVED GROWTH INHIBITOR) (MDGI) [ALIGNMENT] [ABSTRACT] [ABSTRACT] [ABSTRACT] [ABSTRACT] [ABSTRACT] [ABSTRACT] | 1.0e-56 (100%) |
| •HCST8884 HTST41736 | 483 | •Q15699 (sp) BEST! | sp:HOMO SAPIENS CARTILAGE HOMEOPROTEIN 1 (CART-1) [ALIGNMENT] [ABSTRACT] | 2.0e-70 (100%) |
| •HCST8920 HTST41930 | 860 | •P09058 (sp) BEST! | sp:HOMO SAPIENS 40S RIBOSOMAL PROTEIN S8 [ALIGNMENT] [ABSTRACT] [ABSTRACT] [ABSTRACT] | 1.0e-109 (98%) |
| •HCST9106 HTST42746 | 794 | •P35270 (sp) BEST! | sp:HOMO SAPIENS SEPIAPTERIN REDUCTASE (EC 1.1.1.153) (SPR) [ALIGNMENT] [ABSTRACT] | 5.0e-88 (100%) |

FIG.4J

| HCST HTST | LENGTH | ACCESSION NUMBER | DEFINITION | E VALUE (% I.D.) |
|---|---|---|---|---|
| •HCST9207 HTST43157 | 794 | •P25311 (sp) BEST! | sp:HOMO SAPIENS ZINC-ALPHA-2-GLYCOPROTEIN PRECURSOR (ZN-ALPHA-2-GLYCOPROTEIN)(ZN-ALPHA-2-GP)) [ALIGNMENT] [ABSTRACT] [ABSTRACT] [ABSTRACT] [ABSTRACT] | 8.0e-46 (99%) |
| •HCST9308 HTST43558 | 468 | •Q04446 (sp) BEST! | sp:HOMO SAPIENS 1,4-ALPHA-GLUCAN BRANCHING ENZYME (EC 2.4.1.18) (GLYCOGEN BRANCHINGENZYME) (BRANCHERENZYME) [ALIGNMENT] [ABSTRACT] | 7.0e-80 (98%) |
| •HCST9326 HTST43601 | 487 | •P00001 (sp) BEST! | sp:HOMO SAPIENS CYTOCHROME C [ALIGNMENT] [ABSTRACT] [ABSTRACT] | 5.0e-58 (100%) |
| •HCST9368 HTST43766 | 452 | •P35249 (sp) BEST! | sp:HOMO SAPIENS ACTIVATOR 1 37 KD SUBUNIT (REPLICATION FACTOR C 37 KD SUBUNIT) (A137 KD SUBUNIT) (RF-C 37 KD SUBUNIT) (RFC37) [ALIGNMENT] [ABSTRACT] | 1.0e-59 (100%) |
| •HCST9377 HTST43799 | 452 | •P24723 (sp) BEST! | sp:HOMO SAPIENS PROTEIN KINASE C, ETA TYPE (EC 2.7.1.-) (NPKC-ETA) (PKC-L) [ALIGNMENT] [ABSTRACT] [ABSTRACT] | 2.0e-53 (100%) |
| •HCST9447 HTST44113 | 465 | •Q15006 (sp) BEST! | sp:HOMO SAPIENS HYPOTHETICAL PROTEIN KIAA0103 [ALIGNMENT] [ABSTRACT] | 4.0e-51 (100%) |
| •HCST9512 HTST44390 | 644 | •P21851 (sp) BEST! | sp:HOMO SAPIENS BETA-ADAPTIN (PLASMA MEMBRANE ADAPTOR HA2/ AP2 ADAPTIN BETA SUBUNIT)(CLATHRIN ASSEMBLY PROTEIN COMPLEX 2 BETA LARGE CHAIN) (AP105B) [ALIGNMENT] [ABSTRACT] [ABSTRACT] | 2.0e-73 (100%) |
| •HCST9610 HTST44827 | 511 | •P31607 (sp) BEST! | sp:HOMO SAPIENS BTG1 PROTEIN (B-CELL TRANSLOCATION GENE 1 [ALIGNMENT] [ABSTRACT] [ABSTRACT] | 4.0e-68 (99%) |
| •HCST9616 HTST44840 | 555 | •P78406 (sp) BEST! | sp:HOMO SAPIENS MRNA-ASSOCIATED PROTEIN MRNP41 (RAE1 PROTEIN HOMOLOG) [ALIGNMENT] | 3.0e-81 (98%) |
| •HCST9628 HTST44881 | 581 | •P11150 (sp) BEST! | sp:HOMO SAPIENS TRIACYLGLYCEROL LIPASE PRECURSOR (EC 3.1.1.3) (LIPASE, HEPATIC) (HL) [ALIGNMENT] [ABSTRACT] [ABSTRACT] [ABSTRACT] [ABSTRACT] | 2.0e-73 (98%) |
| •HCST9640 HTST44935 | 774 | •P00374 (sp) BEST! | sp:HOMO SAPIENS DIHYDROFOLATE REDUCTASE (EC1.5.1.3) [ALIGNMENT] [ABSTRACT] [ABSTRACT] [ABSTRACT] [ABSTRACT] [ABSTRACT] | 6.0e-88 (99%) |
| •HCST9674 HTST45089 | 449 | •Q08752 (sp) BEST! | sp:HOMO SAPIENS 40 KD PEPTIDYL-PROLYL CIS-TRANS ISOMERASE (EC 5.2.1.8) (PPIASE)(ROTAMASE) (CYCLOPHILIN-40) (CYP-40) (CYCLOPHILIN-RELATED PROTEIN) [ALIGNMENT] [ABSTRACT] [ABSTRACT] | 4.0e-71 (100%) |
| •HCST9701 HTST45272 | 563 | •Q15005 (sp) BEST! | sp:HOMO SAPIENS MICROSOMAL SIGNAL PEPTIDASE 25 KD SUBUNIT (EC 3.4.-.-) (SPC25)(KIAA0102) (FRAGMENT) [ALIGNMENT] [ABSTRACT] | 1.0e-106 (99%) |
| •HCST9838 HTST45938 | 698 | •P15882 (sp) BEST! | sp:HOMO SAPIENS N-CHIMAERIN (NC) (N-CHIMERIN) (ALPHA CHIMERIN) (A-CHIMAERIN) [ALIGNMENT] [ABSTRACT] [ABSTRACT] [ABSTRACT] | 2.0e-87 (96%) |
| •HCST9920 HTST46526 | 419 | •P35270 (sp) BEST! | sp:HOMO SAPIENS CHOLINE KINASE (EC 2.7.1.32) [ALIGNMENT] [ABSTRACT] | 2.0e-61 (98%) |

FIG.4K

| HCST HTST | LENGTH | ACCESSION NUMBER | DEFINITION | E VALUE (% I.D.) |
|---|---|---|---|---|
| •HCST9956 HTST46709 | 484 | •P24539 (sp) BEST! | sp:HOMO SAPIENS ATP SYNTHASE B CHAIN, MITOCHONDRIAL PRECURSOR (EC 3.6.1.34) [ALIGNMENT] [ABSTRACT] | 8.0e-86 (98%) |
| •HCST9974 HTST46803 | 455 | •P17403 (sp) BEST! | sp:SUS SCROFA GLYCOLIPID TRANSFER PROTEIN (GLTP) [ALIGNMENT] [ABSTRACT] | 2.0e-62 (99%) |
| •HCST9996 HTST46936 | 561 | •P08603 (sp) BEST! | sp:HOMO SAPIENS COMPLEMENT FACTOR H PRECURSOR [ALIGNMENT] [ABSTRACT] [ABSTRACT] [ABSTRACT] [ABSTRACT] [ABSTRACT] [ABSTRACT] [ABSTRACT] [ABSTRACT] | 1.0e-109 (97%) |
| •HCST10011 HTST47023 | 610 | •P12429 (sp) BEST! | sp:HOMO SAPIENS ANNEXIN III (LIPOCORTIN III) (PLACENTAL ANTICOAGULANT PROTEIN III)(PAP-III) (35-ALPHA CALCIMEDIN) (INOSITOL 1,2-CYCLIC PHOSPHATE 2-PHOSPHOHYDROLASE) [ALIGNMENT] [ABSTRACT] [ABSTRACT] [ABSTRACT] [ABSTRACT] [ABSTRACT] [ABSTRACT] | 1.0e-97 (98%) |
| •HCST10057 HTST47296 | 498 | •P55822 (sp) BEST! | sp:HOMO SAPIENS SH3BGR PROTEIN (21-GLUTAMIC ACID-RICH PROTEIN) (21-GARP) [ALIGNMENT] [ABSTRACT] | 4.0e-59 (100%) |
| •HCST10094 HTST47442 | 842 | •Q15091 (sp) BEST! | sp:HOMO SAPIENS HYPOTHETICAL PROTEIN KIAA0391 [ALIGNMENT] [ABSTRACT] | 1.0e-143 (96%) |
| •HCST10133 HTST47706 | 459 | •P31152 (sp) BEST! | sp:HOMO SAPIENS EXTRACELLULAR SIGNAL-REGULATED KINASE 4 (EC 2.7.1.-) (ERK4) (MAPKINASE ISOFORM P63) (P63-MAPK) [ALIGNMENT] [ABSTRACT] | 2.0e-84 (97%) |
| •HCST10177 HTST47995 | 603 | •Q05084 (sp) BEST! | sp:HOMO SAPIENS 69 KD ISLET CELL AUTOANTIGEN (ICA69) (ISLET CELL AUTOANTIGEN 1) [ALIGNMENT] [ABSTRACT] | 3.0e-79 (97%) |
| •HCST10207 HTST48261 | 1054 | •P35998 (sp) BEST! | sp:HOMO SAPIENS 26S PROTEASE REGULATORY SUBUNIT 7 (MSS1 PROTEIN) [ALIGNMENT] [ABSTRACT] | 1.0e-147 (95%) |
| •HCST10212 HTST48320 | 516 | •P15170 (sp) BEST! | sp:HOMO SAPIENS G1 TO S PHASE TRANSITION PROTEIN 1 HOMOLOG (GTP-BINDING PROTEINGST1-HS) [ALIGNMENT] [ABSTRACT] | 5.0e-90 (99%) |
| •HCST10228 HTST48400 | 377 | •P06576 (sp) BEST! | sp:HOMO SAPIENS ATP SYNTHASE BETA CHAIN, MITOCHONDRIAL PRECURSOR (EC 3.6.1.34) [ALIGNMENT] [ABSTRACT] [ABSTRACT] [ABSTRACT] [ABSTRACT] | 2.0e-65 (99%) |
| •HCST10230 HTST48413 | 446 | •P16446 (sp) BEST! | sp:RATTUS NORVEGICUS PHOSPHATIDYLINOSITOL TRANSFER PROTEIN ALPHA ISOFORM (PTDINS TRANSFERPROTEIN ALPHA) (PTDINSTP) (PI-TP-ALPHA) [ALIGNMENT] [ABSTRACT] [ABSTRACT] | 1.0e-63 (99%) |
| •HCST10271 HTST48701 | 467 | •P28328 (sp) BEST! | sp:HOMO SAPIENS PEROXISOME ASSEMBLY FACTOR-1 (PAF-1) (PEROXIN-2) (35 KD PEROXISOMALMEMBRANE PROTEIN) [ALIGNMENT] [ABSTRACT] [ABSTRACT] | 2.0e-55 (100%) |
| •HCST10363 HTST49470 | 455 | •P07738 (sp) BEST! | sp:HOMO SAPIENS BISPHOSPHOGLYCERATE MUTASE (EC 5.4.2.4) (2,3-BISPHOSPHOGLYCERATEMUTASE, ERYTHROCYTE) (2,3-BISPHOSPHOGLYCERATE SYNTHASE) (BPGM)(EC 5.4.2.1) (EC 3.1.3.13) (BPG-DEPENDENT PGAM) [ALIGNMENT] [ABSTRACT] [ABSTRACT] [ABSTRACT] | 2.0e-61 (99%) |
| •HCST10366 HTST49478 | 458 | •P27694 (sp) BEST! | sp:HOMO SAPIENS REPLICATION PROTEIN A 70 KD DNA-BINDING SUBUNIT (RP-A) (RF-A)(REPLICATION FACTOR-A PROTEIN 1) (SINGLE-STRANDED DNA-BINDINGPROTEIN) [ALIGNMENT] [ABSTRACT] [ABSTRACT] [ABSTRACT] | 2.0e-60 (99%) |

FIG.4L

CONSTRUCTION OF NORMALIZED CDNA LIBRARIES FROM EUCARYOTIC CELLS

This application claims the benefit of U.S. Provisional Ser. No. 60/095,989, which was filed Aug. 10, 1998.

1.0 FIELD OF THE INVENTION

The present invention relates to a complex cDNA library generated from eukaryotic cells and methods for making such a library. More specifically, the invention uses recombinant constructs that randomly insert into the genome to facilitate the expression of nuclear genes as fusion transcripts. The invention further allows one to specifically subclone the corresponding fusion transcripts into a highly complex cDNA library. The library is easily characterized by molecular analysis techniques, and individual clones can be directly sequenced to generate a sequence database of the cell-derived portion of the fusion transcripts.

2.0 BACKGROUND OF THE INVENTION

The Human Genome Project is currently approaching the sequencing phase of the human genome and the completion of this milestone is expected in the year 2005. The hope is that at the conclusion of the sequencing phase, a comprehensive representation of the human genome will be available for biomedical analysis. However, the resulting sequence data from the human genome project will typically correspond to human genomic sequence, and the actual genes represented in the genomic sequence might not be obvious even with the use of sophisticated computer assisted exon identification programs. The availability of cDNA information will therefore significantly contribute to the value of the sequenced human genome since they directly indicate the presence of transcribed sequences. Thus, the sequencing of cDNA libraries to obtain expressed sequence tags or ESTs that identify exons expressed within a given tissue, cell, or cell line is currently in progress. As a consequence of these efforts, a large number of EST sequences are presently compiled in public and privately held databases. However, the present EST paradigm is inherently limited by the levels and extent of mRNA production within a given cell. A related problem is the lack of cDNA sources from specific tissue and developmental expression profiles. In addition, some genes are typically only active under certain physiological conditions or are generally expressed at levels below or near the threshold necessary for cDNA cloning and detection and are therefore not effectively represented in current cDNA libraries.

Researchers have partially addressed these issues by using phage vectors to clone genomic sequences such that internal exons are trapped (Nehls, et al., 1994, Current Biology, 4(1):983–989, and Nehls, et al., 1994, Oncogene, 9:2169–2175). However, such libraries require the random cloning of genomic DNA into a suitable cloning vector in vitro, followed by reintroduction of the cloned DNA in vivo in order to express and splice the cloned genes prior to producing the cDNA library. Additionally, such methods are limited to "trapping" genes having internal exons.

3.0 SUMMARY OF THE INVENTION

The present invention describes methods for constructing complex cDNA libraries from gene trapped eukaryotic cells. Although the presently described libraries can be constructed from virtually any cell that is naturally capable of splicing nuclear mRNA, animal cells, and particularly mammalian cells, are of particular interest.

Rapid production and sequencing of such normalized gene trapped sequence (GTS) libraries greatly facilitates gene identification and complements current sequencing efforts such as, for example, the Human Genome Project. Accordingly, one embodiment of the present invention is directed to cDNA libraries that provide a normalized representation of the genes present within a given cell, cell line, tissue, plant, or animal. In a preferred embodiment, the GTS libraries are produced by a method that does not include a period of selective culture that enriches the population of eucaryotic cells that incorporate the exogenously introduced gene trap construct.

Accordingly, one embodiment of the present invention is a collection of individually isolated and identified human cDNA sequences that collectively comprise at least one sequence representative of each of the following categories: G-protein coupled recpetors, G proteins, cytoskeletal proteins, protein kinases, steroid response element binding proteins, and tumor suppressor proteins.

The presently described methods for generating such libraries can be used to produce normalized (or equalized) cDNA libraries using mRNA obtained from virtually any eukaryotic cell. Using the described methods, each cell or cell clone is engineered to express a gene, or part of a gene (e.g., sequence), under the control of a promoter that has been nonspecifically, or essentially randomly, integrated into the genome of the target cell. For the purposes of the present invention, the term "nonspecifically integrated" shall mean that a polynucleotide has not specifically integrated into a predefined target sequence, or has not been directed to a particular region of the host cell chromosome by the incorporation of one or more regions of flanking homologous "targeting" DNA.

Given that the production of the mRNA pool that is used to produce the described cDNA libraries is mediated by an exogenously added promoter, the presently described procedures allow one to express a higher percentage of the genes collectively present within the target cell population. An additional feature of the fact that the exogenous promoter element is nonspecifically, or even randomly, integrated into the genome of each cell is that the exogenous promoter more-or-less uniformly directs the expression of the mRNA that is preferentially used to generate the cDNA within the library. The uniformity of this expression effectively "normalizes" the relative percentages of the various cDNAs that are incorporated into the described libraries. In essence, the cDNAs in the library are related by the common promoter element. This feature significantly reduces the burden of sequencing duplicative cDNAs that are typically over represented in conventional cDNA libraries because of differential expression levels within the cell.

A particularly useful feature of the presently described procedure, is that genes that are normally not expressed in the target cell, or expressed at low levels, (i.e., effectively undetectable using conventional methods of generating cDNA), are expressed at levels that allow cDNA production and cloning.

4.0 DESCRIPTION OF THE FIGURES

FIGS. 1A–1D.

FIG. 1A illustrates a retroviral vector that can be used to practice the described invention.

FIG. 1B shows a schematic of how a typical cellular genomic locus is effected by the integration of the retroviral construct into intronic sequences of the cellular gene.

FIG. 1C shows the chimeric transcripts produced by the gene trap event as well as the locations of the binding sites for PCR primers.

FIG. 1D shows how the PCR amplified cDNAs are directionally cloned into a suitable vector.

FIG. 4 presents a representative sampling of "known" genes (identified by name and database, e.g. GENBANK, SWISSPROT, etc, accession number) that have been gene trapped when the described methods were used to produce a human gene trap library.

5.0 DETAILED DESCRIPTION OF THE INVENTION

Figure 2:
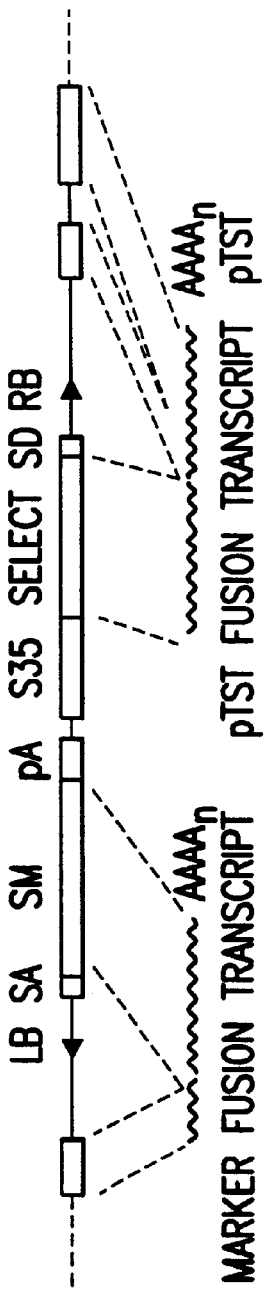
FIG. 2 shows a method of practicing T-DNA mediated high throughput gene trapping in plants using an agrobacterium system.

The present invention relates to normalized "gene trapped" CDNA libraries that provide an enhanced representation of the coding regions, or genes, present within a given cell, cell line, tissue, plant, or animal. The methods used to generate the described libraries exploit several features of the biology of eukaryotic cells and viruses. To produce the described normalized cDNA library, an exogenously added promoter element (incorporated into an appropriately engineered recombinant vector/construct) is introduced into a target cell, tissue, or animal, where the promoter element subsequently integrates into the cellular genome in a nonspecific, or essentially random, manner. For the purposes of the present disclosure, a "normalized" library is characterized as a collection of distinct sequences that are derived from transcripts expressed, or substantially expressed by one or more common exogenously added promoter elements.

Typically, the exogenous promoter element is introduced as part of a 3' gene trap cassette. The 3' gene trap cassette additionally incorporates an exogenously added 3' exon trap that encodes an exon, an operative splice donor site, and does not encode a polyadenylation signal that allows for the efficient polyadenylation of the exogenously added exon. The exon component of the 3' exon trap cassette can encode a selectable marker conferring, for example, antibiotic resistance (i.e., puro or neo, etc.), or the exon can comprise noncoding sequence. The sequence at or near the splice donor region of the 3' exon trap cassette is preferably derived from naturally occurring sequence. More preferably, the 3' exon trap cassette comprises sequence native to, or closely related to sequence derived from the target cell. Preferably, the naturally occurring counterpart of any 3' exon trap cassette sequence is not naturally expressed in the target cell, only poorly expressed, or not expressed at levels sufficient to unduly interfere with the production of the described libraries (as typically detected by northern analysis, or RT-PCR). In the event where the natural counterpart of the described 3' gene trap exon is expressed in the target cell, the exogenously added 3' gene trap exon is preferably engineered to incorporate sequence that is not normally expressed in the target cell.

Any of a wide variety of means can be used to introduce the exogenous promoter element/3' gene trap cassette into the target cell. For example, the 3' gene trap cassette can be introduced using DNA or RNA vectors in conjunction with methods such as, but not limited to, electroporation, lipofection, chemical transfection, infection, nanoparticle delivery, microspheres, etc., and/or any combination thereof.

A preferred method of effecting the essentially random integration of the 3' gene trap cassette is by incorporating the promoter element into a retroviral vector that, after infection, uses the retroviral integration machinery mediate vector integration into the target cell genome. Such biological methods of vector introduction into the target cell and incorporation into the target cell genome are typically more efficient than nonbiological (e.g., chemical, electrical, physical, etc.) means of vector introduction. For example, biological methods of introducing gene trap constructs into target cells allow for the practical application of vector:target cell input ratios of less than about 0.01. Typically, the vector:target cell input ratios (or, as in the case where virus are used, multiplicities of infection, or "m.o.i.") used to practice the present invention will be less than about 1,000, generally less than 500, and often less than 100, 50, 10, or 1. In contrast, nonbiological methods of vector introduction often involve vector:target cell input ratios of 10,000 to 1,000,000 or more. By reducing the ratio of vector to target cell, one reduces the risk that vector concatamers will form in the target cells and hinder sequence acquisition via the formation of vector-to-vector splice products.

After a construct incorporating a 3' gene trap cassette has integrated into the genome, the incorporation of a selectable marker in the construct can allow one to positively identify integration events by pharmacological selection, or other forms of screening (chromogenic or fluorescent assays, and the like). The selectable marker may be expressed by control elements present in the vector, or, preferably, the selectable marker is only expressed under the control of an endogenous, i.e. cellular, promoter. This feature allows one to select for both the integration event, and also better insures that the construct has integrated within a cellular gene. The selectable marker should be sufficiently active to allow cell survival even when expressed at low levels by the endogenous promoter. Given that no selectable marker activity is expected in the absence of such endogenous promoter activity, the genomic integration effectively constitutes a gene trap event. Alternatively, or in addition, a selectable marker can be incorporated into the sequence acquisition component (3' gene trap cassette).

Where gene trap mediated selection is employed to practice the present invention, preferred target cells for the generation of the described libraries include embryonic stem cells, and particularly human embryonic, or other, stem cells. However, in some cases, such as those instances where a relatively high percentage of the endogenous genes within the target cell are inactive, an autonomously expressed selectable marker cassette can optionally be incorporated into the gene targeting vector either upstream or downstream from the 3' gene trap cassette. Where expression of the selectable marker is not dependent upon the gene trap event, the preferential and/or specific cloning feature of the present invention can be exploited to produce the described cDNA libraries without selecting for the gene trap event per se.

Figure 3:
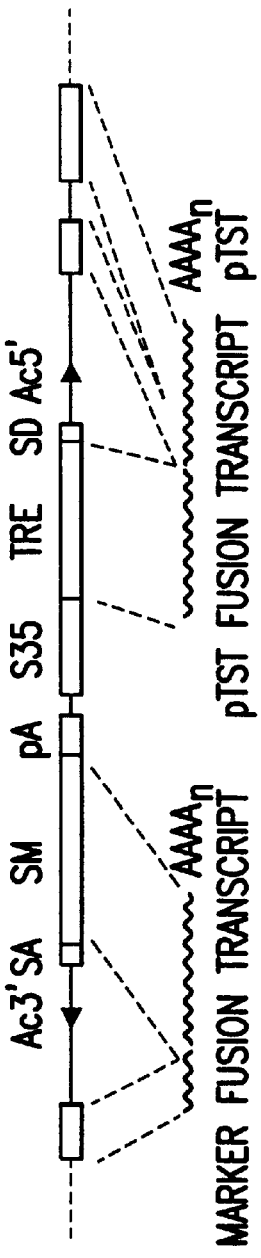
FIG. 3 shows a practicing transposon mediated high throughput gene trapping in plants

Virtually any cell having the cellular machinery necessary to splice nuclear RNA into mRNA, and that can also be manipulated to incorporate exogenous genetic material into the cellular genome, can be used to produce the described GTS libraries. As such, any of a wide variety of eukaryotic cells such as, but not limited to, plant cells (dicots and monocots, angiosperms (poppies, roses, camellias, etc.), gymnosperms (pine, etc.), sorghum, grasses, as well as plants of agricultural significance such as, but not limited to, grains (rice, wheat, corn, millet, oats, etc.), nuts, lentils, chick peas, tubers (potatoes, yams, taro, etc.), herbs, cotton, hemp, coffee, cocoa, tobacco, rye, beets, alfalfa, buckwheat, hay, soy beans, bananas, sugar cane, fruits (citrus and otherwise), grapes, vegetables, and fungi (mushrooms, truffles, etc.), palm, maple, redwood, rape seed, safflower, saffron, coconut yew, oak, and other deciduous and evergreen trees, animal cells, fungal cells, yeast cells, mold cells, and the like can be used to produce the described libraries. Two representative strategies for practicing high throughput gene trapping in plants are provided in FIGS. 2 and 3.

Additional cells of particular interest include, but are not limited to, virtually any primary cell line, isolated tumor cell line, PA-1 human teratocarcinoma cells, HELA cells, fibroblasts, HepB2 cells, Jurkatt cells, transformed cell lines, virally infected cells, transfected cells, stably or transiently transduced cells, stimulated (lectin, cytokine, etc.) cells, irradiated cells, or cell lines from the spleen, bone marrow, germline cells, ovaries, liver, kidney, skin, adrenal gland, neurons, brain, lung, muscle, large and small intestine, bone, secretory glands, stomach, esophagus, trachea, sinus, muscle, or cells or tissues of epithelial, endothelial, mesothelial, ectodermal, endodermal, or mesodermal origin or any combination or mixture thereof. Moreover, infectious virus can be locally or systemically introduced into test animals in vivo, and the described cDNA libraries can be prepared from resected tissues/organs.

Additionally, animal cells or cell lines from bovine, ovine, porcine, canine, avian, and feline species, members of the rodent family, (e.g., mice, rats, as well as rabbits and guinea pigs), members of the genera or families Gallus, Suidae, Bos, Ursus, Meleagris, Capra, Lama, Camelus, Odocoileus, and Oryx, and non-human primates, such as chimpanzees, can be used to practice the present invention.

When retroviral vectors of murine origin are used to construct the described libraries, nonmurine target cells, e.g., human target cells, can be murinized by the addition of a suitable receptor for murine retrovirus. Alternatively, the retroviral gene trap vector(s) can be packaged using a suitable packaging cell line encoding retroviral envelope protein affording amphotropic host specificity. Particularly where human target cells are contemplated, suitable lentiviral gene-trap vectors can be employed using suitable lentiviral packaging cell lines in conjunction with transfecting the suitable virus receptors into the target cells. Similarly, avian retroviruses can be adapted as described herein and used to directly prepare cDNA libraries from avian cells. Alternatively, pantropic virus/packaging cell lines can be employed.

Another feature of the described 3' gene trap cassette is that the exogenous promoter drives high levels of transcription of the trapped gene. As a result, the fusion transcript expressed by the exogenously added promoter contains sequences from both the transgenic construct and downstream genomic sequences. The portion of the fusion transcript derived from the transgenic construct can additionally encode, but not necessarily so, a selectable marker that would allow one to select for cells that contain functional transcripts. Where vector introduction into the target cell is sufficiently efficient (as in the case with viral infection), one need not select (by antibiotic resistance, selective growth advantage, fluorescence activated screening or cell sorting, etc.) for target cells expressing vector sequences. Thus, a particularly preferred embodiment of the present invention include methods of gene trapping vectors where the exon component of the 3' gene trap cassette does not encode a selectable or amplifiable marker sequence. Since the majority of selectable marker sequences are not native to eucaryotic cells, the absence of a selectable marker sequence can also materially increase the splicing efficiency of the unpaired splice donor of the 3' gene trap cassette.

FIG. 1A illustrates a typical vector suitable for the practice of the present invention, in this case a retroviral vector. An appropriately packaged retrovirus containing the retroviral transgenic construct is used to infect a mammalian cell and subsequently integrate the construct into the cellular genome. FIG. 1B shows a schematic of how a typical cellular genomic locus is effected by the integration of the retroviral construct into intronic sequences of the cellular gene (generating two chimeric transcripts). As illustrated in FIG. 1C, the first chimeric transcript is a fusion between the coding region of the resistance marker carried within the transgenic construct and the upstream exon(s) from the cellular gene. A mature transcript is generated when the indicated splice donor (SD) and splice acceptor (SA) sites are spliced. Translation of this fusion transcript produces the protein encoded by the resistance marker and allows for the positive selection of the gene trapped cell.

Another chimeric transcript is shown in FIG. 1C. This transcript is a fusion between the first exon (EXON1) of the transgenic construct and downstream exons from the cellular gene. Again, the mature transcript is generated by proper splicing between the indicated SD and SA sites. The construct encoded promoter element drives the transcription of the first (transgenic construct encoded) exon that contains unique sequence that permits the selective enrichment of the fusion transcript using molecular biological methods such as, for example, the polymerase chain reaction (PCR). These sequences serve as unique primer binding sites for EXON1-specific PCR amplification of the transcript and one or several rare-cutter endonuclease restriction sites to allow site-specific cloning. These features allow one to efficiently and selectively clone the transgene induced fusion transcripts from pools of mammalian cells as opposed to the majority of cell-specific transcripts.

Based on the unique sequence present in EXON1, that is schematically indicated as a rare-cutter (A) restriction site in FIG. 1B, selective cloning of the fusion transcript is achieved as shown in FIG. 1D. cDNA is generated by reverse transcribing isolated RNA (i.e., total RNA or mRNA) from pools of cells that have undergone independent gene trap events using, for example, cDNA-1 as a deoxyoligonucleotide primer. The 3' end of the cDNA-1 primer consists of a homopolymeric stretch of deoxythymidine residues that bind to the polyadenylated end of the mRNA. At its 5' end, the oligonucleotide contains a sequence that can serve as a binding site for primer PCR-2. In the center, cDNA-1 contains the sequence of a second rare-cutter (B) restriction site. Depending on the size of the pool and the transcriptional levels of the fusion transcript, second strand synthesis is carried out either with deoxyoligonucleotide primer cDNA-2 using Klenow polymerase or by a polymerase chain reaction (PCR) in the presence of primers PCR-1 and PCR-2.

The second strand reaction products that are generated by PCR (in the case where fusion transcripts are present in low abundance) or by a simple second strand synthesis are digested with restriction endonucleases that recognize their corresponding restriction site (e.g., A and B). Where longer PCR products are desired, the templates can be size selected prior to PCR. Additionally, PCR conditions can be suitably modified using any of a variety of established procedures for enhancing the size of the PCR products. Such methods are described, inter alia, in U.S. Pat. No. 5,556,772, and/or the PanVera (Madison, Wis.) New Technologies for Biomedical Research catalog (1997/98) both of which are herein incorporated by reference.

Optionally, prior to cloning the cDNA fragments can be size-selected using conventional methods such as, for example, chromatography, electrophoresis, and the like. The cleaved cDNAs are directionally cloned into a new lambda phage vector (see FIG. 1D) or virtually any other cloning vector/vehicle (generically referred to as trapped sequence tag vectors "TST vectors" in FIG. 1D), preferably incorporating a multiple cloning site with restriction sites corresponding to those incorporated into the amplified cDNAs. After cloning, the resulting phage/vectors can be handled as a conventional cDNA library using standard procedures. Individual colonies and/or plaques can be used to generate templates for DNA sequencing reactions, and can be used as templates for further amplification by PCR using the SEQ-1 and SEQ-2 primers indicated in FIG. 1D. Such amplicons, or GTSs, are easily subjected to sequencing analysis and can further serve as gene specific probes for obtaining full-length genes.

The presently described methods are amenable to the production of large numbers of gene trap clones. The large quantities of clones that can be generated can quantitatively compensate for aspects of gene trapping technology that are qualitatively less efficient. For example, 5' RACE is a powerful tool that can be used to discover the 5' end of genes. However, typical versions of 5' RACE only include a unique PCR primer at the 3' end of the PCR product (typically hybridizing to sequence unique to the 5' gene trap cassette) and must rely on "snap back" or random primers to prime the 5' region of the PCR product. The lack of specific priming at the 5' end of the PCR product creates a variety of complications that effect the direct detection and analysis of 5' RACE products. By cloning the 5' RACE products into traditional cloning vectors, the shear numbers of clones that can be generated and easily screened compensates for the inherent inefficiencies of 5' RACE, and renders practical the large scale automated discovery of sequences defining the 5' ends of genes.

Given that the host cell splicing machinery is exploited during the production of the described normalized cDNA libraries, the SD and/or SA sequences, and preferably the flanking exon and or intron sequences, encoded by the described gene trap constructs are derived from eukaryotic cells, typically from cells of the same phylum as the target cells, more typically from cells from the same order, preferably from cells of the same genus, and more preferably from cells of the same-species, or any mixture, combination, or variation of the above. Optionally, the SD, SA, and/or exon sequences can be either naturally occurring or engineered "consensus" sequences optimized for splicing efficiency in specific target cells, or a broad spectrum of potential target cells. Alternatively, the splicing control sequences can be engineered to target splicing to specific genes or gene families, or to preferentially avoid specific genes or gene families.

To ensure maximum coverage of the genome, the target cells are preferably trapped using one or more vectors incorporating 5' gene trap cassettes, 3' gene trap cassettes, and internal exon traps, either singly or in combination. This feature is further applicable to exon trapped phage libraries, and, as such, an additional embodiment of the present invention relates to cDNA libraries conceptually similar to those described by Nehls et al. (1994, Current Biology, 4(1):983–989, and 1994, Oncogene, 9:2169–2175 both of which are herein incorporated by reference in their entirety) that additionally employ phage vectors incorporating 3' exon traps and/or 5' exon traps, or any mixture thereof, to produce the phage genomic DNA library used to subsequently generate the trapped cDNA library.

A typical 3' exon trap cassette to be incorporated into such vectors comprises in operable combination, a promoter element, an exon expressed by the promoter that encodes an operative splice donor sequence, a cloning site for the insertion of genomic DNA inserts located 3' to the splice donor, and does not include an exogenously engineered polyadenylation sequence operably positioned to allow the polyadenylation of a cloned genomic exon. Similarly, a typical 5' exon trap cassette to be incorporated into such vectors comprises, in operable combination, a cloning site for the insertion of genomic DNA inserts, an exon encoding an operative splice acceptor site located 3' to the cloning site, a polyadenylation sequence located 3' to the splice acceptor site, and is not engineered to include a vector encoded splice donor sequence operably positioned to allow efficient (as opposed to cryptic) splicing with the splice acceptor site of the vector encoded exon. Particularly where a 5' exon trap is employed, unique sequences within the flanking phage sequence and 5' exon trap cassette can be amplified by RT-PCR to rapidly produce and analyze 5' RACE products either directly or after the generation of a 5' RACE cDNA library. This embodiment of the present invention also allows for the automated detection of sequences defining the 5' ends of naturally occurring eukaryotic genes. Similar 5' RACE cDNA libraries can additionally be constructed using internal exon traps.

The promoters used to generate the described normalized cDNA libraries are preferably derived from eukaryotic cells, typically from cells of the same phylum as the target cells, more typically from cells from the same order, preferably from cells of the same genus, and more preferably from cells of the same species, or any mixture, combination, or variation of the above. Optionally, the promoters can be either naturally occurring or engineered "consensus" promoters optimized for expression in specific target cells, or a broad spectrum of potential target cells. Alternatively, the splicing control sequences can be engineered to preferentially or inducibly express specific genes or gene families, or to preferentially or inducibly avoid the expression of specific genes or gene families. Where the inducible or regulatable expression of target cell genes is desired, the transgenic constructs can optionally be engineered to encode suitable regulatory regions (transcription factor binding sites, response elements, etc.) operably positioned relative to the promoter region.

Typically, the described transgenic constructs can be introduced to the target cells at any of a wide variety of ratios (or multiplicities of infection where viral vectors are used to infect cells). Typically, such ratios will start at about 0.001 vector/target cells, generally the ratios are between about 0.01 or 1.0 and about several hundred or thousand vectors/target cell, or more, as only limited by the properties of the mode of vector introduction. Ideally, the transgenic constructs are introduced to the target cells such that the target cell genome is collectively saturated with gene trap constructs. Given the high efficiencies of some methods of introducing genetic material into cells (i.e., high titer retroviral infection), in conjunction with the fact that the described methods allow for the preferential cloning of gene trapped sequences, the described cDNA libraries can be constructed without the need for selecting for gene trapped cells. The omission of selection substantially simplifies and expedites the generation of the described libraries. Where DNA transfection, lipofection, electroporation, etc. are employed to introduce the 3' gene trap to the target cell, the vectors are optionally linearized and/or concatamerized prior to addition to the target cell.

Using the presently described methods, normalized libraries of at least about 100 distinct vector expressed cDNA sequences are produced, typically at least about 1,000 distinct cDNA sequences, generally, at least about 3,000 distinct cDNA sequences, more generally at least about 7,500 distinct cDNA sequences, preferably at least about 20,000 distinct cDNA sequences, more preferably at least about 50,000 distinct cDNA sequences, and specifically at least about 100,000. Depending on the size of the genome, the number of distinct cDNAs represented in the library can number from up to about several dozen thousand, several hundred thousand, one million, or more, as only limited by practical considerations and the number of exons present in the target cell genome.

The present invention is further illustrated by the following examples, which are not intended to be limiting in any way whatsoever.

6.0. EXAMPLES
6.1 Construction of Gene Trapped cDNA Libraries

Normalized GTS cDNA libraries were produced as follows. Pools of modified human PA-1 teratocarcinoma cells (e.g., PA-2, PA-1 cells that have been transfected to express the murine ecotropic retrovirus receptor) were typically infected with a suitable gene trap retrovirus at an m.o.i between about 0.01 and about 0.1 (although much higher m.o.i.'s such as 1 to more than 10 could have been used). The retrovirus (described in greater detail in U.S. application Ser. No. 09/057,328, herein incorporated by reference) is shown in FIG. 1A. FIG. 1B schematically shows how the target cell genomic locus is presumably mutated by the integration of the retroviral construct into intronic sequences present in the cellular gene. The integration of the retroviral vector results in the generation of two chimeric transcripts. As illustrated in FIG. 1C, the first chimeric transcript is a fusion between the coding region of the resistance marker (where applicable, neo was used to produce the presently described GTSs) carried within the transgenic construct and the upstream exon(s) from the cellular gene. A mature transcript is generated when the indicated splice donor (SD) and splice acceptor (SA) sites are spliced. Translation of this fusion transcript produces the protein encoded by the resistance marker and allows for selection of gene trapped target cells, although selection is not required to produce the described GTSs. By the foregoing selection, GTSs are generated in a substantially more rapid and cost-efficient manner, and gene trapped sequences can be obtained that are independent of whether the target cell expresses the "trapped" gene.

Another chimeric transcript is shown in FIG. 1C. This transcript is a fusion between the first exon of the transgenic construct (EXON1—the first exon of the murine btk gene was used as the sequence acquisition component for the described GTSs) and downstream exons from the cellular genome. Unlike the transcript encoding the selectable marker exon, the transcript encoding EXON1 is transcribed under the control of a vector encoded, and hence exogenously added, promoter (such as the PGK promoter), and the corresponding mRNA is generated by splicing between the indicated SD ("unpaired," within the vector) and SA sites. The region encoding the sequence acquisition exon (EXON1) has also been engineered to incorporate a unique sequence that permits the selective enrichment of the fusion transcript using molecular biological methods such as, for example, the polymerase chain reaction (PCR). These sequences serve as unique primer binding sites for EXON1-specific PCR amplification of the transcript and can additionally incorporate one or several rare-cutter endonuclease restriction sites to allow site-specific cloning. These features allow for the efficient and preferential cloning of transgene expressed fusion transcripts from pools of target cells relative to the background of cellularly encoded transcripts.

Based on the unique sequence present in EXON1, that is schematically indicated as a rare-cutter (A) restriction site in FIG. 1B, selective cloning of the fusion transcript is achieved as shown in FIG. 1D. cDNA was generated by reverse transcribing isolated RNA from pools of cells that have undergone independent gene trap events. The second strand reaction products that were generated by PCR were digested with restriction endonucleases that recognize their corresponding restriction site(s) (e.g., A and B). Additionally, PCR conditions were suitably modified using a variety of established procedures for enhancing the size of the PCR products. Such methods are described, inter alia, in U.S. Pat. No. 5,556,772, and/or the PanVera (Madison, WI) New Technologies for Biomedical Research catalog (1997/98) both of which are herein incorporated by reference.

Prior to cloning, the PCR cDNA fragments were size-selected using conventional methods such as, for example, chromatography, gel-electrophoresis, and the like. Alternatively or in addition to this size selection, the PCR templates could have been previously size selected into separate template pools.

After digestion with suitable restriction enzymes, and size selection as described above, the cleaved cDNAs were directionally cloned into phage vectors (see FIG. 1D), although any other cloning vector/vehicle could have been used. Such vectors are generically referred to as gene trapped sequence vectors (see "TST vector" in FIG. 1D), preferably incorporating a multiple cloning site with restriction sites corresponding to those incorporated into the amplified cDNAs (e.g., Sfi I, which allows for directional cloning of the cDNAs). After cloning, the resulting phage were handled as a conventional cDNA library using standard procedures. Individual colonies and/or plaques were picked and used to generate PCR derived (using the primers indicated below) templates for DNA sequencing reactions.

A more detailed description of the above follows. The btk retroviral gene trap vector described above was introduced into human PA-2 cells (or murine ES cells) using standard techniques. In brief, vector/virus containing supernatant from GP+E or AM12 packaging cells was added to approximately 50,000 cells (at an input ratio between about 0.01 and about 0.1 virus/target cell) for between about 16 to about 24 hours, and the cells were subsequently selected with G418 at active concentration of about 400 micrograms/ml for about 9–10 days. Between about 600 and about 3,000 G418 resistant colonies were subsequently pooled, and subjected to RNA isolation, reverse transcription, PCR, restriction digestion, size selection, and subcloning into lambda phage vectors. Individual phage plaques were directly amplified, purified, and sequenced to obtain the corresponding GTS.

When the described normalized cDNA libraries were generated without any use of selection pressure subsequent to vector introduction, about $1\times10^6$ cells (PA-2, Hela, HepG2, or Jurkatt cells) per 100 mm dish were plated and infected with AM12 packaged btk retrovirus at an m.o.i. of approximately 0.01. After a 16 h incubation, the cells were washed in PBS and grown in culture media for four days. RNA from each plate was extracted, reverse transcribed, and the resulting cDNA was subject to two rounds of PCR, each for 25 cycles. The resulting PCR products were digested with Sfi and separated by gel electrophoresis. Six size fractions (between about 300 and about 4,000 bp) were recovered and each fraction was ligated into lambdaGT10Sfi arms, in vitro packaged, and plated for lysis. Individual plaques were picked from the plates, subject to an additional round of PCR, and subsequently sequenced to obtain the described GTSs. The particulars are described in greater detail below.

FIG. 1D shows the chimeric fusion transcript that is formed when the first exon of the transgenic construct (EXON1—the first exon of the murine btk gene was used as the sequence acquisition component for the described GTSs) is spliced to downstream exons from the cellular genome. Unlike the transcript encoding the selectable marker exon, the transcript encoding EXON1 is transcribed under the control of a vector encoded, and hence exogenously added, promoter (such as the PGK promoter), and the corresponding mRNA is generated by splicing between the indicated SD and SA sites.

The region encoding the sequence acquisition exon (EXON1) has also been engineered to incorporate a unique sequence that permits the selective enrichment of the fusion transcript using molecular biological methods such as, for example, the polymerase chain reaction (PCR). These sequences serve as unique primer binding sites for EXON1-specific PCR amplification of the transcript and can additionally incorporate one or several rare-cutter endonuclease restriction sites to allow site-specific cloning. These features allow for the efficient and preferential cloning of transgene expressed fusion transcripts from pools of target cells relative to the background of cellularly encoded transcripts.

Based on the unique sequence present in EXON1, that is schematically indicated as a rare-cutter (A) restriction site in FIG. 1B, selective cloning of the fusion transcript is achieved as shown in FIG. 1D. cDNA was generated by reverse transcribing isolated RNA from pools of cells that have undergone independent gene trap events using, for example, RTT-1 as a deoxyoligonucleotide primer. The 3' end of the RTT-1 primer consisted of a homopolymeric stretch of deoxythymidine residues that bound to the polyadenylated end of the mRNA. At its 5' end, the oligonucleotide contained a sequence that can serve as a binding site for a second and a third primer (GET-2 and GET-2N). In the center, RTT-1 contains the sequence of a second rare-cutter (B) restriction site. Depending on the size of the pool and the transcriptional levels of the fusion transcript, second strand synthesis was carried out either with deoxyoligonucleotide primer BTK-1 using Klenow polymerase or by a polymerase chain reaction (PCR) in the presence of primers BTK-1 and GET-2. The second strand reaction products that were generated by PCR were digested with restriction endonucleases that recognize their corresponding restriction site (e.g., A and B). Additionally, PCR conditions were suitably modified using a variety of established procedures for enhancing the size of the PCR products. Such methods are described, inter alia, in U.S. Pat. No. 5,556,772, and/or the PanVera (Madison, Wis.) New Technologies for Biomedical Research catalog (1997/98) both of which are herein incorporated by reference.

Prior to cloning, the PCR cDNA fragments were size-selected using conventional methods such as, for example, chromatography, gel-electrophoresis, and the like. Alternatively or in addition to this size selection, the PCR templates could have been previously size selected into separate template pools.

After digestion with suitable restriction enzymes, and size selection as described above, the cleaved cDNAs were directionally cloned into phage vectors (see FIG. 1D), although any other cloning vector/vehicle could have been used. Such vectors are generically referred to as gene trapped sequence vectors, or "GTS vectors" in FIG. 1D), preferably incorporating a multiple cloning site with restriction sites corresponding to those incorporated into the amplified cDNAs (e.g., Sfi I, which allows for directional cloning of the cDNAs). After cloning, the resulting phage were handled as a conventional cDNA library using standard procedures. Individual colonies and/or plaques were picked and used to generate PCR derived (using the primers indicated below) templates for DNA sequencing reactions.

Total cell RNA isolation was conducted using RNAzol (Friendswood, Tex., 77546) per the manufacturer's specifications. An RT premix containing 2× First Strand buffer, 100 mM Tris-HCl, pH 8.3, 150 mM KCl, 6 mM $MgCl_2$, 2 mM dNTPs, RNAGuard (1.5 units/reaction, Pharmacia), 20 mM DTT, RTT-1 primer (3 pmol/rxn, GenoSys Biotechnologies, sequence: 5' tggctaggccccaggataggcctcgctggccttttttttttttttt 3', SEQ ID NO:1) and Superscript II enzyme (200 units/rxn, Life Technologies) was added. The plate/tube was transferred to a thermal cycler for the RT reaction (37° C. for 5 min. 42° C. for 30 min. and 55° C. for 10 min).

The cDNA was amplified using two distinct, and preferably nested, stages of PCR. The PCR premix contained: 1.1× MGBII buffer (74 mM Tris pH 8.8, 18.3 mM Ammonium Sulfate, 7.4 mM $MgCl_2$, 5.5 mM 2ME, 0.011% Gelatin), 11.1% DMSO (Sigma), 1.67 mM τdNTPS, Taq (5 units/rxn), water and primers. The sequences of the first round primers are: BTK-1 5' gccatggctccggtaggtccagag 3', SEQ ID NO:2 (GET-2, 5' tggctaggccccaggatag 3', SEQ ID NO:3), (about 7 pmol/rxn). The sequences of the second round primers are BTK-4 5' gtccagagatggccatagc 3', SEQ ID NO:4 (GET-2N 5' ccaggataggcctcgctg 3', SEQ ID NO:5), (used at about 20 pmol/rxn). The outer premix was added to an aliquot of CDNA and run for 20 cycles (94° C. for 45 sec., 56° C. for 60 sec 72° C. for 2–4 min). An aliquot of this product was added to the inner premix and cycled at the same temperatures 20 times.

The PCR products of the second amplification series were extracted using phenol/chloroform, chloroform, and isopropanol precipitated in the presence of glycogen/sodium acetate. After centrifugation, the nucleic acid pellets were washed with 70 percent ethanol and were resuspended in TE, pH 8. After digestion with Sfi I at 55° C., the digested products were loaded onto 0.8% agarose gels and size-selected using DEAE membranes as described (Sambrook et al., 1989, supra). Generally, six approximate size-fractions (<700 bp, 700–900 bp, 900–1,300 bp, 1,300–1,600 bp, 1,600–2,000 bp, >2,000 bp) were separately ligated into GTS vector arms that were engineered to contain the corresponding Sfi I "A" and "B" specific overhangs (i.e., TAG and GCG, respectively). The ligation products were packaged using commercially available lambda packaging extracts (Promega), and plated using E. coli strain C600 using conventional procedures (Sambrook et al., 1989, supra). Individual plaques were directly picked into 40 microliters of PCR buffer and subjected to 35 cycles of PCR [at 94° C. for 45 sec., 56° C. for 60 sec 72° C. for 1–3 min (depending on the size fraction)] using 12 pmol of the primers SEQ-4, 5' tacagtttttcttgtgaagattg 3', SEQ ID NO:6 and SEQ-5, 5' gggtagtccccacctttg 3', SEQ ID NO:7, per PCR reaction. The cloned 3' RACE products were purified using an S300 column equilibrated in STE essentially as described in Nehls et al., 1993, TIG,9:336–337, and the products were recovered by centrifugation at 1,200×g for 5 min. This step removes unincorporated nucleotides, oligonucleotides, and primer-dimers. The PCR products were subsequently applied to a 0.25 ml bed of Sephadex® G-50 (DNA Grade, Pharmacia Biotech AB) that was equilibrated in MilliQ $H_2O$, and recovered by centrifugation as described above. Purified PCR products were quantified by fluorescence using PicoGreen (Molecular Probes, Inc., Eugene Oregon) as per the manufacturer's instructions.

Dye terminator cycle sequencing reactions with Ampli-Taq® FS DNA polymerase (Perkin Elmer Applied Biosystems, Foster City, Calif.) were carried out using 7 pmoles of primer (oligonucleotide BTK-3; 5' tccaagtcctg-gcatctcac 3', SEQ ID NO:8) and approximately 30–120 ng of 3' template. Unincorporated dye terminators were removed from the completed sequencing reactions using G-50 columns as described above. The reactions were dried under vacuum, resuspended in loading buffer, and electrophoresed through a 6% Long Ranger acrylamide gel (FMC BioProducts, Rockland, Me.) on an ABI Prism® 377 with XL upgrade as per the manufacturer's instructions.

When the resulting sequences were analyzed, a significant proportion of the resulting cDNA sequences were novel when compared known polynucleotide sequence information. Moreover, the a wide variety of known genes were "hit" including, for example, transmembrane proteins, secreted proteins, G-protein coupled receptors, G proteins and other signaling proteins, G activating proteins, steroid response element binding proteins, protein kinases and phosphatases, helicases and DNA modifying enzymes, proteases, transporter proteins, protease inhibitors, cytokines, interferons, blood proteins, cytoskeletal proteins, transcription factors, metabolic enzymes, ubiquitin conjugating enzymes, cell cycle regulators, tumor suppressors, oncogenes, immunoglobulins, CD surface proteins, immune receptors, chemokines, autoantigens, tyrosine kinases, genes that mediate apoptosis, etc. A sampling of the additional genes that have been hit using the disclosed is presented in FIG. 4 which also provides the name and database (i.e., GENBANK, SWISSPROT, etc.) accession numbers of the hit genes. Given the wide spectrum of genes that can be rapidly trapped and identified using the disclosed technology, an additional embodiment of the present invention includes a collection of individually isolated gene trapped normalized and chimeric cDNA sequences that collectively comprise at least one polynucleotide sequence corresponding to a gene representative of each of the above categories, or any subset or combination of at least about four of the disclosed categories.

6.2. Nonhuman Gene Trapped cDNA Libraries

The above methods were also employed using canine cell lines (ATCC strain D22, bone, carcinoma; collie), murine ES cells (LEX-1), and porcine cell lines (ATCC strains LLC-PK1 (porcine kidney) or ST (swine testis)) using the methods for generating GTSs without selection essentially as described above. In brief, approximately $1 \times 10^6$ animal cells per 100 mm dish were plated and infected with AM12 packaged btk retrovirus at a m.o.i. of approximately 0.01. After a 16 h incubation the cells were washed in PBS and grown in M15 media under conditions that do not select for cells having integrated vector sequences for about four days (i.e., without selection). RNA from each plate was extracted, reverse transcribed, and the resulting cDNA was subject to two rounds of PCR, each for 25 cycles. The resulting PCR products were digested with Sfi and separated by gel electrophoresis. Six size fractions (between about 300 and about 4,000 bp) were recovered and each fraction was ligated into lambdaGT10Sfi arms, in vitro packaged, and plated for lysis. Individual plaques were picked from the plates, subject to an additional round of PCR, and subsequently sequenced to obtain porcine or canine GTSs. The resulting murine, canine, and porcine GTSs proved the broad applicability of the described technology to a variety of mammalian species.

The present invention is not to be limited in scope by the specific embodiments described herein, which are intended as specific illustrations of individual aspects of the invention, and functionally equivalent methods and components are within the scope of the invention. Indeed, various modifications of the invention, in addition to those shown and described herein will become apparent to those skilled in the art from the foregoing description and accompanying figures. Such modifications are intended to fall within the scope of the appended claims.

All patents, patent applications, and references cited in this application are herein incorporated by reference in their entirety.

What is claimed is:

1. A method for producing a normalized cDNA library derived from eukaryotic cells, comprising the steps of:
   a) introducing a recombinant vector containing a promoter sequence into eukaryotic target cells at an input ratio of less than about 100;
   b) maintaining the target cells under conditions to allow the vector to integrate into the target cell genome;
   c) isolating total RNA from said target cells to produce cDNA; and
   d) cloning the cDNA from step (c) into a vector; whereby a cDNA library is produced having at least about 100 distinct and isolated chimeric cDNAs each comprising vector encoded sequence linked to naturally occurring cellular exon sequence.

2. The method of claim 1 wherein said eukaryotic cell is an animal cell.

3. The method of claim 2 wherein said animal cell is a vertebrate cell.

4. The method of claim 3 wherein said vertebrate cell is a mammalian cell.

5. The method of claim 4 wherein said mammalian cell is a human cell.

6. The method of claim 4 wherein said mammalian cell is a mouse cell.

7. The method of claim 4 wherein said mammalian cell is a pig cell.

8. The method of claim 4 wherein said mammalian cell is a dog cell.

9. The method of claim 5 wherein said cDNA library comprises a sequence corresponding to at least one of each of the following genes:
   a) G-protein coupled receptor;
   b) a protein kinase;
   c) a transporter protein;
   d) a tRNA synthase; and
   e) an annexin II.

* * * * *

SEQUENCE LISTING

```
<160> NUMBER OF SEQ ID NOS:  8

<210> SEQ ID NO 1
<211> LENGTH: 40
<212> TYPE: DNA
<213> ORGANISM: Artificial Sequence
<220> FEATURE:
<223> OTHER INFORMATION: Primer

<400> SEQUENCE: 1
tggctaggcc ccaggatagg cctcgctggc cttttttttt                           40

<210> SEQ ID NO 2
<211> LENGTH: 24
<212> TYPE: DNA
<213> ORGANISM: Artificial Sequence
<220> FEATURE:
<223> OTHER INFORMATION: Primer

<400> SEQUENCE: 2
gccatggctc cggtaggtcc agag                                            24
```

```
<210> SEQ ID NO 3
<211> LENGTH: 19
<212> TYPE: DNA
<213> ORGANISM: Artificial Sequence
<220> FEATURE:
<223> OTHER INFORMATION: Primer

<400> SEQUENCE: 3
tggctaggcc ccaggatag                                                  19

<210> SEQ ID NO 4
<211> LENGTH: 19
<212> TYPE: DNA
<213> ORGANISM: Artificial Sequence
<220> FEATURE:
<223> OTHER INFORMATION: Primer

<400> SEQUENCE: 4
gtccagagat ggccatagc                                                  19

<210> SEQ ID NO 5
<211> LENGTH: 18
<212> TYPE: DNA
<213> ORGANISM: Artificial Sequence
<220> FEATURE:
<223> OTHER INFORMATION: Primer

<400> SEQUENCE: 5
ccaggatagg cctcgctg                                                   18

<210> SEQ ID NO 6
<211> LENGTH: 23
<212> TYPE: DNA
<213> ORGANISM: Artificial Sequence
<220> FEATURE:
<223> OTHER INFORMATION: Primer

<400> SEQUENCE: 6
tacagttttt cttgtgaaga ttg                                             23

<210> SEQ ID NO 7
<211> LENGTH: 19
<212> TYPE: DNA
<213> ORGANISM: Artificial Sequence
<220> FEATURE:
<223> OTHER INFORMATION: Primer

<400> SEQUENCE: 7
gggtagtccc cacctttg                                                   19

<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8
tccaagtcct ggcatctcac                                                 20
```